United States Patent
Lorenzo et al.

(10) Patent No.: US 9,632,097 B2
(45) Date of Patent: Apr. 25, 2017

(54) DETERMINING PATHOLOGICAL CARTILAGE TURNOVER

(71) Applicant: Nordic Boiscience A/S, Herlev (DK)

(72) Inventors: Pilar Lorenzo, Lund (SE); Patrik Önnerfjord, Lund (SE); Emma Åhrman, Lomma (SE); Dick Heinegård

(73) Assignee: Nordic Boiscience A/S, Herlev (DK)

( * ) Notice: Subject to any disclaimer, the term of this patent is extended or adjusted under 35 U.S.C. 154(b) by 0 days.

(21) Appl. No.: 14/411,046

(22) PCT Filed: Jun. 27, 2013

(86) PCT No.: PCT/SE2013/050809
§ 371 (c)(1),
(2) Date: Dec. 23, 2014

(87) PCT Pub. No.: WO2014/003679
PCT Pub. Date: Jan. 3, 2014

(65) Prior Publication Data
US 2015/0301065 A1    Oct. 22, 2015

Related U.S. Application Data

(60) Provisional application No. 61/690,525, filed on Jun. 28, 2012.

(51) Int. Cl.
| | | |
|---|---|---|
| *G01N 31/00* | (2006.01) | |
| *G01N 33/53* | (2006.01) | |
| *G01N 33/68* | (2006.01) | |
| *C07K 14/78* | (2006.01) | |
| *C07K 16/28* | (2006.01) | |
| *C07K 14/47* | (2006.01) | |
| *C07K 16/18* | (2006.01) | |
| *G01N 27/62* | (2006.01) | |

(52) U.S. Cl.
CPC ......... *G01N 33/6887* (2013.01); *C07K 14/47* (2013.01); *C07K 14/78* (2013.01); *C07K 16/18* (2013.01); *C07K 16/28* (2013.01); *G01N 27/62* (2013.01); *G01N 33/6878* (2013.01); *C07K 2317/34* (2013.01); *G01N 2333/47* (2013.01); *G01N 2800/105* (2013.01)

(58) Field of Classification Search
CPC ........ C07K 14/47; C07K 14/78; C07K 16/18; C07K 16/28; C07K 2317/34; G01N 33/6887; G01N 33/6878; G01N 27/62; G01N 2333/47; G01N 2800/105
See application file for complete search history.

(56) References Cited

U.S. PATENT DOCUMENTS

| | | | | |
|---|---|---|---|---|
| 4,795,702 A | * | 1/1989 | Blake | G01N 33/571 435/23 |
| 5,124,252 A | * | 6/1992 | Guerrant | G01N 33/56972 435/7.24 |
| 5,387,504 A | * | 2/1995 | Mumford | C07K 14/4713 424/94.67 |
| 7,211,649 B1 | * | 5/2007 | Heinegard | C07K 14/47 435/325 |
| 7,812,125 B2 | * | 10/2010 | Lorenzo | C07K 14/78 424/520 |
| 7,892,768 B2 | * | 2/2011 | Danfelter | C07K 14/78 422/1 |
| 8,580,529 B2 | * | 11/2013 | Danfelter | C07K 14/78 422/430 |
| 8,663,944 B2 | * | 3/2014 | Lorenzo | C07K 14/78 435/7.93 |
| 2008/0318337 A1 | * | 12/2008 | Heinegard | C07K 14/78 436/501 |
| 2009/0232822 A1 | * | 9/2009 | Joseloff | G01N 33/57423 424/139.1 |

FOREIGN PATENT DOCUMENTS

| | | |
|---|---|---|
| WO | WO 98/07035 | 2/1998 |
| WO | WO 2005/116658 A2 | 12/2005 |
| WO | WO 2011/102908 A2 | 8/2011 |
| WO | WO 2011/109738 A1 | 9/2011 |
| WO | WO 2012/078760 A1 | 6/2012 |
| WO | WO 2014/003679 A1 | 1/2014 |

OTHER PUBLICATIONS

Di Cesare et al., 1996. Increased degradation and altered tissue distribution of cartilage oligomeric matrix protein in human rheumatoid and osteoarthritic cartilage. J. Orthopaedic Res. 14: 946-955.*
Lohmander et al., 1994. Release of cartilage oligomeric matrix protein (COMP) into joint fluid after knee injury and in osteoarthritis. Ann. Rheumatic Dis. 53: 8-13.*
Zhen et al., 2008. Characterization of metalloproteinase cleavage products of human articular cartilage. Arthritis & Rheumatism 58: 2420-2431.*
Newton et al., 1994. Characterization of human and mouse cartilage oligomeric matrix protein. Genomics 24: 435-439.*
Dickinson et al., 2003. Cleavage of cartilage oligomeric matrix protein (thrombospondin-5) by matrix metalloproteinases and a disintegrin and metalloproteinase with thrombospondin motifs. Matrix Biol. 22: 267-278.*
Ganu et al., 1998. Inhibition of interleukin-1alpha-induced cartilage oligomeric matrix protein degradation in bovine articular cartilage by matrix metalloproteinase inhibitors. Arthritis & Rheumatism 41: 2143-2151.*
Stracke et al., 2000. Matrix metalloproteinases 19 and 20 cleave aggrecan and cartilage oligomeric matrix protein (COMP). FEBS Lett. 478: 52-56.*

(Continued)

*Primary Examiner* — Lisa Cook
(74) *Attorney, Agent, or Firm* — Benjamin Aaron Adler

(57) ABSTRACT

The present embodiments relate to methods for determining or detecting pathological cartilage turnover by detection of Cartilage Oligomeric Matrix Protein (COMP) neoepitopes, both released into body fluids and present in the tissue. Furthermore the embodiments relate to antibodies against COMP neoepitopes and to fragments and peptides containing COMP neoepitopes for generation of such antibody.

8 Claims, 4 Drawing Sheets

(56) References Cited

OTHER PUBLICATIONS

Hughes et al., 1992. Monoclonal antibodies recognizing protease-generated neoepitopes from cartilage proteoglycan degradation. J. Biol. Chem. 267: 16011-16014.*

Goldenberg et al., 2005. Biochemical markers for the prediction of preterm birth. Am J. Obstet. Gynecol. 192: S36-S46.*

Fossang, AJ et al., Neoepitopes as biomarkers of cartilage catabolism, Inflamm. res 52:277-282 (2003).

Lai, Y et al., Enhanced COMP catabolism detected in serum of patients with arthritis and animal disease modesl through a novel . . . , Osteoarth. & Cartilage 20:854-862 (2012).

Neidhart, M et al., Small fragments of cartilage oligomeric matrix protein in synovial fluid and serum as markers for cartilage . . . , Brit. J. Rheumatogy 36:1151-1160 (1997).

Tenson, T et al., Erythromycin resistance peptides selected from random peptide libraries, J. Biol. Chem. 272(28):17425-17430 (1997).

* cited by examiner

DETERMINING PATHOLOGICAL CARTILAGE TURNOVER

TECHNICAL FIELD

The present embodiments generally relate to determining, detecting or monitoring pathological cartilage turnover, and in particular to the usage of selected Cartilage Oligomeric Matrix Protein (COMP) fragmentation neoepitopes capable of differentiating between pathological cartilage turnover and benign or normal cartilage turnover.

BACKGROUND

Pathological conditions resulting in tissue degradation such as cartilage degradation constitute a major medical, social and economical problem. Of persons older than 65 years of age, about 50% of the population in the Western world has arthritis. Tissue degradation processes are characterized by destruction of tissues by the breakdown of its components. The tissue components can be degraded due to enzymes, often proteases, or by toxic compounds. For this reason, determination of tissue degradation processes for the purpose of diagnosis, disease monitoring, treatment etc. can be performed by numerous methods. One way to determine degradation processes in connective tissue diseases, such as arthritic conditions, arteriosclerosis, degenerative joint conditions etc., is the detection of formation and presence of degradation products of the connective tissue components. This allows direct detection of the degradation process, compared to indirect methods as e.g. loss of tissue, inflammation, swelling and presence of autoreactive autoantibodies, which have been widely employed in the diagnosis of joint disease, such as arthritic conditions.

Traditionally, the clinical diagnosis of arthritis is based on the patient's history, physical examination, radiographs and measures of inflammation inducing autoantibodies. The prognosis, treatment and clinical outcome of patients with arthritis are assessed by serial determinations. However, in order to minimize permanent tissue damage caused by pathological conditions involving cartilage degeneration, it is important to be able to diagnose such conditions at an early stage. Accordingly, during the last decade efforts have been made to find suitable biological markers that enable an early detection of pathological cartilage degeneration.

Elevated serum levels of COMP have previously been associated with ongoing joint destruction in rheumatoid arthritis (Månsson et al, J. Clin. Invest (1995), vol. 95, pp 1077-1077; Wollheim et al., British Journal of Rheumatology (1997), vol. 36, pp 847-849; Petersson et al., British Journal of Rheumatology (1998), vol. 37, pp 46-50). Significant amounts of fragments of COMP have also been found in synovial fluid from patients with rheumatoid arthritis and other forms of inflammatory arthritis (Neidhardt et al., British Journal of Rheumatology (1997), vol. 36, pp 1151-1160).

It has also been suggested to use COMP or nucleic acid sequences encoding COMP for preparing a pharmaceutical composition for preventing and/or treating arthritic conditions in a mammal (WO 98/46253). Accordingly, COMP can be regarded as a key compound when diagnosing and/or treating different forms of arthritis.

COMP has previously been used as a marker of cartilage turnover (Saxne et al., British Journal of Rheumatology (1992), vol. 31, pp. 583-591). Lai et al., (Osteoarthritis Cartilage (2012), vol. 20, pp 854-862) developed a sandwich ELISA where serum COMP fragments are used for monitoring the arthritic progression. They show difference in serum COMP levels between arthritic patients and non-arthritic control subjects.

A method for determining a tissue degradation process by detection of neoepitopes is disclosed in WO 2005/116658, where neoepitopes that appear after cleavage of COMP between 625 and 626 of the amino acid sequence of COMP are used.

In Söderlin M. (2003) *A population-based study on early arthritis in southern Sweden. Incidence, preceding infections, diagnostic markers and economic burden.* Doctoral dissertation, Linköping University, Department of Molecular and Clinical Medicine COMP is used as a marker, but could not show any statistical difference between different diagnosis groups and even in the control group 18% of the patients had elevated COMP levels.

The results of the methods used today, for diagnosis and monitoring of diseases such as for example arthritis, show a great overlap between disease and non-disease patients as a result of high background from normal tissue turnover.

A major limitation with the prior methods and techniques is that they are not able to distinguish between pathological cartilage turnover from normal turnover, due to high background levels from normal cartilage turnover. Hence, there are still room for improvements within the technical field.

SUMMARY

It is a general objective to determine pathological cartilage turnover in a sample.

It is a particular objective to provide methods and tools enabling distinguish between pathological cartilage turnover and normal or benign cartilage turnover.

These and other objectives are met by embodiments defined herein.

An aspect of the embodiments relates to a method of determining pathological cartilage turnover. The method comprises detecting, in a sample, presence of at least one neoepitope of mammalian Cartilage Oligomeric Matrix Protein (COMP). The at least one neoepitope is formed by cleavage of the mammalian COMP at least one cleavage site selected from a group consisting of between position 77 ($S^{77}$) and position 78 ($V^{78}$); position 88 ($L^{88}$) and position 89 ($L^{89}$); position 90 ($H^{90}$) and position 91 ($C^{91}$); position 104 ($Q^{104}$) and position 105 ($T^{105}$); position 190 ($N^{190}$) and position 191 ($C^{191}$); position 194 ($N^{194}$) and position 195 ($S^{195}$); position 226 ($Q^{226}$) and position 227 ($R^{227}$); position 531 ($F^{531}$) and position 532 ($R^{532}$); position 554 ($L^{554}$) and position 555 ($N^{555}$); position 574 ($Y^{574}$) and position 575 ($T^{575}$); position 577 ($F^{577}$) and position 578 ($N^{578}$); position 657 ($T^{657}$) and position 658 ($G^{658}$); position 691 ($Q^{691}$) and position 692 ($V^{692}$), position 710 ($N^{710}$) and position 711 ($V^{711}$); and position 725 ($F^{725}$) and position 726 ($C^{726}$) of the amino acid sequence of said mammalian COMP as defined in SEQ ID NO: 1, or any combination thereof. The method also comprises determining presence of pathological cartilage turnover if the at least one neoepitope is detected in the sample.

Another aspect of the embodiments relates to an isolated C-terminally truncated fragment of mammalian COMP. In this aspect, a C-terminal of the fragment is amino acid 77 of SEQ ID NO: 1, and the fragment comprises at least three consecutive amino acids of SEQ ID NO: 18 starting from a C-terminal of SEQ ID NO: 18 and extending towards an N-terminal of SEQ ID NO: 18;

a C-terminal of the fragment is amino acid 88 of SEQ ID NO: 1, and the fragment comprises at least three consecutive amino acids of SEQ ID NO: 19 starting from a C-terminal of SEQ ID NO: 19 and extending towards an N-terminal of SEQ ID NO: 19;

a C-terminal of the fragment is amino acid 90 of SEQ ID NO: 1, and the fragment comprises at least three consecutive amino acids of SEQ ID NO: 20 starting from a C-terminal of SEQ ID NO: 20 and extending towards an N-terminal of SEQ ID NO: 20;

a C-terminal of the fragment is amino acid 104 of SEQ ID NO: 1, and the fragment comprises at least three consecutive amino acids of SEQ ID NO: 21 starting from a C-terminal of SEQ ID NO: 21 and extending towards an N-terminal of SEQ ID NO: 21;

a C-terminal of the fragment is amino acid 190 of SEQ ID NO: 1, and the fragment comprises at least three consecutive amino acids of SEQ ID NO: 22 starting from a C-terminal of SEQ ID NO: 22 and extending towards an N-terminal of SEQ ID NO: 22;

a C-terminal of the fragment is amino acid 194 of SEQ ID NO: 1, and the fragment comprises at least three consecutive amino acids of SEQ ID NO: 23 starting from a C-terminal of SEQ ID NO: 23 and extending towards an N-terminal of SEQ ID NO: 23;

a C-terminal of the fragment is amino acid 226 of SEQ ID NO: 1, and the fragment comprises at least three consecutive amino acids of SEQ ID NO: 24 starting from a C-terminal of SEQ ID NO: 24 and extending towards an N-terminal of SEQ ID NO: 24;

a C-terminal of the fragment is amino acid 531 of SEQ ID NO: 1, and the fragment comprises at least three consecutive amino acids of SEQ ID NO: 25 starting from a C-terminal of SEQ ID NO: 25 and extending towards an N-terminal of SEQ ID NO: 25;

a C-terminal of the fragment is amino acid 554 of SEQ ID NO: 1, and the fragment comprises at least three consecutive amino acids of SEQ ID NO: 26 starting from a C-terminal of SEQ ID NO: 26 and extending towards an N-terminal of SEQ ID NO: 26;

a C-terminal of the fragment is amino acid 574 of SEQ ID NO: 1, and the fragment comprises at least three consecutive amino acids of SEQ ID NO: 27 starting from a C-terminal of SEQ ID NO: 27 and extending towards an N-terminal of SEQ ID NO: 27;

a C-terminal of the fragment is amino acid 577 of SEQ ID NO: 1, and the fragment comprises at least three consecutive amino acids of SEQ ID NO: 28 starting from a C-terminal of SEQ ID NO: 28 and extending towards an N-terminal of SEQ ID NO: 28;

a C-terminal of the fragment is amino acid 657 of SEQ ID NO: 1, and the fragment comprises at least three consecutive amino acids of SEQ ID NO: 29 starting from a C-terminal of SEQ ID NO: 29 and extending towards an N-terminal of SEQ ID NO: 29;

a C-terminal of the fragment is amino acid 691 of SEQ ID NO: 1, and the fragment comprises at least three consecutive amino acids of SEQ ID NO: 30 starting from a C-terminal of SEQ ID NO: 30 and extending towards an N-terminal of SEQ ID NO: 30;

a C-terminal of the fragment is amino acid 710 of SEQ ID NO: 1, and the fragment comprises at least three consecutive amino acids of SEQ ID NO: 31 starting from a C-terminal of SEQ ID NO: 31 and extending towards an N-terminal of SEQ ID NO: 31; or a C-terminal of the fragment is amino acid 725 of SEQ ID NO: 1, and the fragment comprises at least three consecutive amino acids of SEQ ID NO: 32 starting from a C-terminal of SEQ ID NO: 32 and extending towards an N-terminal of SEQ ID NO: 32.

A further aspect of the embodiments relates to an isolated N-terminally truncated fragment of mammalian COMP. In this aspect, an N-terminal of the fragment is amino acid 78 of SEQ ID NO: 1, and the fragment comprises at least three consecutive amino acids of SEQ ID NO: 33 starting from an N-terminal of SEQ ID NO: 33 and extending towards a C-terminal of SEQ ID NO: 33;

an N-terminal of the fragment is amino acid 89 of SEQ ID NO: 1, and the fragment comprises at least three consecutive amino acids of SEQ ID NO: 34 starting from an N-terminal of SEQ ID NO: 34 and extending towards a C-terminal of SEQ ID NO: 34;

an N-terminal of the fragment is amino acid 91 of SEQ ID NO: 1, and the fragment comprises at least three consecutive amino acids of SEQ ID NO: 35 starting from an N-terminal of SEQ ID NO: 35 and extending towards a C-terminal of SEQ ID NO: 35;

an N-terminal of the fragment is amino acid 105 of SEQ ID NO: 1, and the fragment comprises at least three consecutive amino acids of SEQ ID NO: 36 starting from an N-terminal of SEQ ID NO: 36 and extending towards a C-terminal of SEQ ID NO: 36;

an N-terminal of the fragment is amino acid 191 of SEQ ID NO: 1, and the fragment comprises at least three consecutive amino acids of SEQ ID NO: 37 starting from an N-terminal of SEQ ID NO: 37 and extending towards a C-terminal of SEQ ID NO: 37;

an N-terminal of the fragment is amino acid 195 of SEQ ID NO: 1, and the fragment comprises at least three consecutive amino acids of SEQ ID NO: 38 starting from an N-terminal of SEQ ID NO: 38 and extending towards a C-terminal of SEQ ID NO: 38;

an N-terminal of the fragment is amino acid 227 of SEQ ID NO: 1, and the fragment comprises at least three consecutive amino acids of SEQ ID NO: 39 starting from an N-terminal of SEQ ID NO: 39 and extending towards a C-terminal of SEQ ID NO: 39;

an N-terminal of the fragment is amino acid 532 of SEQ ID NO: 1, and the fragment comprises at least three consecutive amino acids of SEQ ID NO: 40 starting from an N-terminal of SEQ ID NO: 40 and extending towards a C-terminal of SEQ ID NO: 40;

an N-terminal of the fragment is amino acid 555 of SEQ ID NO: 1, and the fragment comprises at least three consecutive amino acids of SEQ ID NO: 41 starting from an N-terminal of SEQ ID NO: 41 and extending towards a C-terminal of SEQ ID NO: 41;

an N-terminal of the fragment is amino acid 575 of SEQ ID NO: 1, and the fragment comprises at least three consecutive amino acids of SEQ ID NO: 42 starting from an N-terminal of SEQ ID NO: 42 and extending towards a C-terminal of SEQ ID NO: 42;

an N-terminal of the fragment is amino acid 578 of SEQ ID NO: 1, and the fragment comprises at least three consecutive amino acids of SEQ ID NO: 43 starting from an N-terminal of SEQ ID NO: 43 and extending towards a C-terminal of SEQ ID NO: 43;

an N-terminal of the fragment is amino acid 658 of SEQ ID NO: 1, and the fragment comprises at least three consecutive amino acids of SEQ ID NO: 44 starting from an N-terminal of SEQ ID NO: 44 and extending towards a C-terminal of SEQ ID NO: 44;

an N-terminal of the fragment is amino acid 692 of SEQ ID NO: 1, and the fragment comprises at least three consecutive amino acids of SEQ ID NO: 45 starting from an N-terminal of SEQ ID NO: 45 and extending towards a C-terminal of SEQ ID NO: 45;

an N-terminal of the fragment is amino acid 711 of SEQ ID NO: 1, and the fragment comprises at least three consecutive amino acids of SEQ ID NO: 46 starting from an N-terminal of SEQ ID NO: 46 and extending towards a C-terminal of SEQ ID NO: 46; or an N-terminal of the fragment is amino acid 726 of SEQ ID NO: 1, and the fragment comprises at least three consecutive amino acids of SEQ ID NO: 47 starting from an N-terminal of SEQ ID NO: 47 and extending towards a C-terminal of SEQ ID NO: 47.

Yet another aspect of the embodiments relates to a conjugate configured to be used for production of antibodies against at least one neoepitope of mammalian COMP. The at least one neoepitope is formed by cleavage of the mammalian COMP at least one cleavage site selected from a group consisting of between position 77 ($S^{77}$) and position 78 ($V^{78}$); position 88 ($L^{88}$) and position 89 ($L^{89}$); position 90 ($H^{90}$) and position 91 ($C^{91}$); position 104 ($Q^{104}$) and position 105 ($T^{105}$); position 190 ($N^{190}$) and position 191 ($C^{191}$); position 194 ($N^{194}$) and position 195 ($S^{195}$); position 226 ($Q^{226}$) and position 227 ($R^{227}$); position 531 ($F^{531}$) and position 532 ($R^{532}$); position 554 ($L^{554}$) and position 555 ($N^{555}$); position 574 ($Y^{574}$) and position 575 ($T^{575}$); position 577 ($F^{577}$) and position 578 ($N^{578}$); position 657 ($T^{657}$) and position 658 ($G^{658}$); position 691 ($Q^{691}$) and position 692 ($V^{692}$), position 710 ($N^{710}$) and position 711 ($V^{711}$); and position 725 ($F^{725}$) and position 726 ($C^{726}$) of the amino acid sequence of the mammalian COMP as defined in SEQ ID NO: 1, or a combination thereof. The conjugate comprises at least one isolated C-terminally truncated fragment according to above and/or at least one isolated N-terminally truncated fragment according to above coupled to or admixed with a peptide carrier.

A further aspect of the embodiments relates to the use of an isolated C-terminally truncated fragment according to above, an isolated N-terminally truncated fragment according to above and/or a conjugate according to above for production of antibodies that specifically bind to at least one neoepitope formed by cleavage of mammalian COMP at least one cleavage site selected from a group consisting of between position 77 ($S^{77}$) and position 78 ($V^{78}$); position 88 ($L^{88}$) and position 89 ($L^{89}$); position 90 ($H^{90}$) and position 91 ($C^{91}$); position 104 ($Q^{104}$) and position 105 ($T^{105}$); position 190 ($N^{190}$) and position 191 ($C^{191}$); position 194 ($N^{194}$) and position 195 ($S^{195}$); position 226 ($Q^{226}$) and position 227 ($R^{227}$); position 531 ($F^{531}$) and position 532 ($R^{532}$); position 554 ($L^{554}$) and position 555 ($N^{555}$); position 574 ($Y^{574}$) and position 575 ($T^{575}$); position 577 ($F^{577}$) and position 578 ($N^{578}$); position 657 ($T^{657}$) and position 658 ($G^{658}$); position 691 ($Q^{691}$) and position 692 ($V^{692}$), position 710 ($N^{710}$) and position 711 ($V^{711}$); and position 725 ($F^{725}$) and position 726 ($C^{726}$) of the amino acid sequence of the mammalian COMP as defined in SEQ ID NO: 1, or a combination thereof.

Still another aspect of the embodiments relates to a method for production of antibodies that specifically bind to at least one neoepitope formed by cleavage of mammalian COMP at least one cleavage site selected from a group consisting of between position 77 ($S^{77}$) and position 78 ($V^{78}$); position 88 ($L^{88}$) and position 89 ($L^{89}$); position 90 ($H^{90}$) and position 91 ($C^{91}$); position 104 ($Q^{104}$) and position 105 ($T^{105}$); position 190 ($N^{190}$) and position 191 ($C^{191}$); position 194 ($N^{194}$) and position 195 ($S^{195}$); position 226 ($Q^{226}$) and position 227 ($R^{227}$); position 531 ($F^{531}$) and position 532 ($R^{532}$); position 554 ($L^{554}$) and position 555 ($N^{555}$); position 574 ($Y^{574}$) and position 575 ($T^{575}$); position 577 ($F^{577}$) and position 578 ($N^{578}$); position 657 ($T^{657}$) and position 658 ($G^{658}$); position 691 ($Q^{691}$) and position 692 ($V^{692}$), position 710 ($N^{710}$) and position 711 ($V^{711}$); and position 725 ($F^{725}$) and position 726 ($C^{726}$) of the amino acid sequence of the mammalian COMP as defined in SEQ ID NO: 1, or a combination thereof. The method comprises raising antibodies against an isolated C-terminally truncated fragment according to above, an isolated N-terminally truncated fragment according to above and/or a conjugate according to above and isolating the antibodies.

A further aspect of the embodiments relates to an isolated antibody against an isolated C-terminally truncated fragment according to above, an isolated N-terminally truncated fragment according to above and/or a conjugate according to above. The isolated antibody specifically binds to at least one neoepitope formed by cleavage of mammalian COMP at least one cleavage site selected from a group consisting of between position 77 ($S^{77}$) and position 78 ($V^{78}$); position 88 ($L^{88}$) and position 89 ($L^{89}$); position 90 ($H^{90}$) and position 91 ($C^{91}$); position 104 ($Q^{104}$) and position 105 ($T^{105}$); position 190 ($N^{190}$) and position 191 ($C^{191}$); position 194 ($N^{194}$) and position 195 ($S^{195}$); position 226 ($Q^{226}$) and position 227 ($R^{227}$); position 531 ($F^{531}$) and position 532 ($R^{532}$); position 554 ($L^{554}$) and position 555 ($N^{555}$); position 574 ($Y^{574}$) and position 575 ($T^{575}$); position 577 ($F^{577}$) and position 578 ($N^{578}$); position 657 ($T^{657}$) and position 658 ($G^{658}$); position 691 ($Q^{691}$) and position 692 ($V^{692}$), position 710 ($N^{710}$) and position 711 ($V^{711}$); and position 725 ($F^{725}$) and position 726 ($C^{726}$) of the amino acid sequence of the mammalian COMP as defined in SEQ ID NO: 1, or a combination thereof.

A related aspect of the embodiments defines an isolated antibody according to above for use in determining pathological cartilage turnover.

The present embodiments are able to determine or detect presence of pathological cartilage turnover in sample from a mammalian subject, preferably a human subject. In more detail, the embodiments can be used to distinguish normal, healthy individuals with normal cartilage turnover from individuals with a pathological cartilage and COMP turnover caused by a disease.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Figure 1:
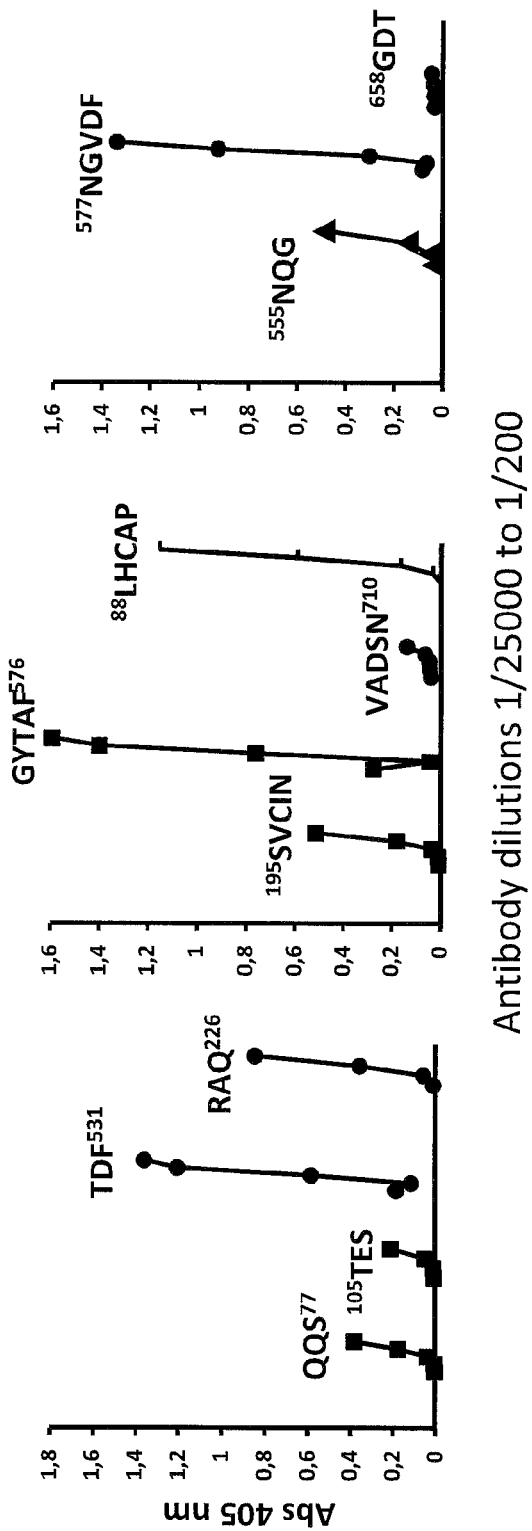
FIG. 1 shows titrations of COMP cleavage antibodies.

The present embodiments generally relate to determining, detecting or monitoring pathological cartilage turnover. The present embodiments in particular relate to the usage of special neoepitopes of mammalian Cartilage Oligomeric Matrix Protein (COMP) that are specific for pathological or pathogenic cartilage turnover.

Hence, the neoepitopes of the present embodiments are able to distinguish between a subject, preferably a mammalian subject and more preferably a human subject, suffering from a disease causing pathological cartilage turnover from a subject having normal cartilage turnover.

The normal cartilage turnover is also referred herein to as benign or background cartilage turnover. Such benign cartilage turnover generally occurs in all cartilaginous tissue and is part of the normal adaptation of these tissues to load and environment. Hence, this benign cartilage turnover is not due a harmful tissue breakdown or a disease but is rather a natural process taking place in the subject.

The prior art techniques of using COMP and COMP neoepitopes discussed in the background section have shortcomings in terms of not being able to distinguish between the normal, benign cartilage turnover and pathological cartilage turnover. For instance, Saxne et al., British Journal of Rheumatology (1992), vol. 31, pp 583-591 and Lai et al., Osteoarthritis Cartilage (2012), vol. 20, pp 854-862 detect background signal even in control subjects. In clear contrast to these prior art techniques, the present embodiments make use of certain neoepitopes not present in normal cartilage breakdown. Accordingly, these unique neoepitopes provide a very good tool for detecting or monitoring pathological cartilage turnover or breakdown. Furthermore, WO 2005/116658 used neoepitopes that appear after cleavage of COMP between 625 and 626 of the amino acid sequence of COMP for determining a tissue degradation process. However the neoepitopes in WO 2005/116658 cannot be used to distinguish between normal COMP or cartilage turnover and pathological COMP or cartilage turnover. Hence, the neoepitopes in WO 2005/116658 are used for determining tissue degradation in general and cannot be used for specific monitoring of pathological cartilage turnover.

One problem with today's assays of COMP in body fluids that target general epitopes for diagnosis and monitoring of joint disease and tissue breakdown is that there is a background turnover in particularly all cartilaginous tissues that is part of the normal adaptation of these tissues to load and environment. As a result, the increased breakdown occurring in a particular joint cartilage in disease can only be seen against a background of normal turnover. Thus, the increase is only on top of an existing level. It is, however, desirable to identify facts about the fragments that distinguish the pathological ones from those normally present. The embodiments herein solve this problem by focusing on neoepitopes not present in normal cartilage turnover.

Thus, the inventors have surprisingly showed that there are specific cleavage sites in pathological cartilage turnover that are not present in normal cartilage turnover. This means that new epitopes that are not normally exposed on COMP appears after cleavage of the protein in subjects suffering from a disease causing pathological cartilage turnover. These new epitopes or neoepitopes are, however, not formed in healthy subjects with only benign cartilage turnover. These new neoepitopes of the embodiments can therefore be used in improved methods and techniques for determining, detecting and monitoring pathological cartilage turnover in disease.

Herein, pathological/benign cartilage turnover and pathological/benign COMP are used interchangeable and both imply a pathological/normal process in which cartilage is broken down causing increased serum level of COMP.

The present embodiments disclose a method for determining, measuring or monitoring pathological cartilage or COMP turnover. Neoepitopes from specific fragmentations that are detected, measured or monitored are not present as a result of normal turnover, which makes the embodiments unique and it is therefore possible to distinguish normal turnover from turnover in disease. This is a valuable tool when diagnosing diseases including, but not limited to, osteoarthritis (OA), rheumatoid arthritis (RA), reactive arthritis (ReA), psoriatic arthritis, juvenile chronic arthritis, cardiovascular disease, tendon disease, osteoporosis, osteomalacia, fracture repair, arteriosclerosis, scleroderma, fibrotic skin or trauma, such as joint trauma.

Since the neoepitopes of embodiments are practically not present in normal, non-disease, individuals this will provide for novel and early diagnoses of disease processes. The present embodiments therefore relates to methods for detecting or monitoring pathological cartilage turnover and the use of this method for distinguishing a patient with pathological turnover from non-diseased individuals with normal cartilage turnover. The method comprises detecting or monitoring the presence of specific COMP fragmentation neoepitopes in a sample. This will provide for novel and early diagnoses of disease processes which could be used to follow disease progression longitudinally within a patient. The embodiments could also be used to follow the efficacy upon various potential treatments.

The neoepitopes of the present embodiments are thereby formed by cleavage of the amino acid sequence of COMP (SEQ ID NO: 1) at specific positions in subjects suffering from a disease causing pathological cartilage turnover.

Neoepitope as used herein is an epitope that is not normally exposed on COMP but appears after changes of the protein, due to cleavage of the protein. The neoepitope may, for example, be formed by a primary, secondary and/or tertiary structure of a COMP fragment appearing after cleavage.

The sequences presented below are from human COMP, but the embodiments also encompass non-human, mammalian subjects, such as horse, dog, mouse, rat, guinea pig and primates. COMP sequences from these non-human mammals are so similar to human COMP that antibodies directed towards neoepitopes in human COMP may crossreact with corresponding neoepitopes in the non-human, mammalian COMP and vice versa.

The sequence of human COMP is presented below and can be found in SEQ ID NO: 1.

```
MVPDTACVLL LTLAALGASG QGQSPLGSDL GPQMLRELQE

TNAALQDVRE LLRQQVREIT FLKNTVMECD ACGMQQSVRT

GLPSVRPLLH CAPGFCFPGV ACIQTESGAR CGPCPAGFTG

NGSHCTDVNE CNAHPCFPRV RCINTSPGFR CEACPPGYSG

PTHQGVGLAF AKANKQVCTD INECETGQHN CVPNSVCINT

RGSFQCGPCQ PGFVGDQASG CQRRAQRFCP DGSPSECHEH

ADCVLERDGS RSCVCAVGWA GNGILCGRDT DLDGFPDEKL

RCPERQCRKD NCVTVPNSGQ EDVDRDGIGD ACDPDADGDG

VPNEKDNCPL VRNPDQRNTD EDKWGDACDN CRSQKNDDQK

DTDQDGRGDA CDDDIDGDRI RNQADNCPRV PNSDQKDSDG

DGIGDACDNC PQKSNPDQAD VDHDFVGDAC DSDQDQDGDG
```

-continued

```
HQDSRDNCPT VPNSAQEDSD HDGQGDACDD DDDNDGVPDS

RDNCRLVPNP GQEDADRDGV GDVCQDDFDA DKVVDKIDVC

PENAEVTLTD FRAFQTVVLD PEGDAQIDPN WVVLNQGREI

VQTMNSDPGL AVGYTAFNGV DFEGTFHVNT VTDDDYAGFI

FGYQDSSSFY VVMWKQMEQT YWQANPFRAV AEPGIQLKAV

KSSTGPGEQL RNALWHTGDT ESQVRLLWKD PRNVGWKDKK

SYRWFLQHRP QVGYIRVRFY EGPELVADSN VVLDTTMRGG

RLGVFCFSQE NIIWANLRYR CNDTIPEDYE THQLRQA
```

The present embodiments disclose a method for distinguishing pathological turnover from normal cartilage turnover, comprising detecting or monitoring in a sample the presence of the specific COMP fragmentation neoepitopes presented herein. To detect or monitor these neoepitopes any possible method may be used, including but not limited to Multiple Reaction Monitoring (MRM), ELISA or any other suitable immunoassay as known in the art.

The embodiments further disclose the specific neoepitopes created by the cleavages and antibodies against these novel neoepitopes.

The inventors disclose new cleavages sites of COMP (SEQ ID NO: 1) where the neoepitopes to our surprise is not present or detected at significantly lower levels in normal cartilage breakdown. This provides a unique tool to really distinguish disease from non-disease.

The specific cleavage neoepitopes of COMP present in pathological cartilage turnover but not present in normal cartilage turnover are formed by cleavage of COMP at least one cleavage site selected from a group consisting of between position 77 ($S^{77}$) and 78 ($V^{78}$); 88 ($L^{88}$) and 89 ($L^{89}$); 90 ($H^{90}$) and 91 ($C^{91}$); 104 ($Q^{104}$) and 105 ($T^{105}$); 190 ($N^{190}$) and 191 ($C^{191}$); 194 ($N^{194}$) and 195 ($S^{195}$); 226 ($Q^{226}$) and 227 ($R^{227}$); 531 ($F^{531}$) and 532 ($R^{532}$); 554 ($L^{554}$) and 555 ($N^{555}$); 574 ($Y^{574}$) and 575 ($T^{575}$); 577 ($F^{577}$) and 578 ($N^{578}$); 657 ($T^{657}$) and 658 ($G^{658}$); 691 ($Q^{691}$) and 692 ($V^{692}$); 710 ($N^{710}$) and 711 ($V^{711}$) and 725 ($F^{725}$) and 726 ($C^{726}$).

Accordingly, an aspect of the embodiments relates to a method of determining pathological cartilage turnover. The method comprises detecting, in a sample, presence of at least one neoepitope of mammalian COMP, preferably human COMP. The at least one neoepitope is formed by cleavage of the mammalian COMP, preferably human COMP, at least one cleavage site selected from a group consisting of between position 77 ($S^{77}$) and position 78 ($V^{78}$); position 88 ($L^{88}$) and position 89 ($L^{89}$); position 90 ($H^{90}$) and position 91 ($C^{91}$); position 104 ($Q^{104}$) and position 105 ($T^{105}$); position 190 ($N^{190}$) and position 191 ($C^{191}$); position 194 ($N^{194}$) and position 195 ($S^{195}$); position 226 ($Q^{226}$) and position 227 ($R^{227}$); position 531 ($F^{531}$) and position 532 ($R^{532}$); position 554 ($L^{554}$) and position 555 ($N^{555}$); position 574 ($Y^{574}$) and position 575 ($T^{575}$); position 577 ($F^{577}$) and position 578 ($N^{578}$); position 657 ($T^{657}$) and position 658 ($G^{658}$); position 691 ($Q^{691}$) and position 692 ($V^{692}$), position 710 ($N^{710}$) and position 711 ($V^{711}$); and position 725 ($F^{725}$) and position 726 ($C^{726}$) of the amino acid sequence of the mammalian COMP, preferably human COMP, as defined in SEQ ID NO: 1, and any combination thereof. The method also comprises determining presence of pathological cartilage turnover if the at least one neoepitope is detected in the sample.

Hence presence of at least one neoepitope formed by cleavage of COMP at specific cleavage sites as defined above is an indicator of pathological cartilage and COMP turnover in the sample.

A variant of this aspect relates to a method of detecting pathological cartilage turnover in a mammalian subject, preferably a human subject. The method comprises contacting a sample from the mammalian subject with at least one antibody that specifically binds to at least one neoepitope of mammalian COMP according to the embodiments. The method also comprises detecting, in the sample and based on the at least one antibody, presence of the at least one neoepitope. In this method the presence of the at least one neoepitope indicates that the mammalian subject has or is suffering from cartilage turnover.

Another variant of this aspect relates to a method detecting pathological cartilage turnover in a mammalian subject, preferably a human subject. The method comprises contacting a sample from the mammalian subject with at least one antibody directed to an isolated C-terminally truncated fragment of mammalian COMP as defined herein or an isolated N-terminally truncated fragment of the mammalian COMP as defined herein or a conjugate as defined herein, or any combination thereof. The method also comprises detecting, in the sample and based on the at least one antibody, presence of at least one fragment formed by cleavage of mammalian COMP as defined herein. In this method the presence of the at least one fragments indicates that the mammalian subject has or is suffering from cartilage turnover.

Yet another aspect of this aspect relates to a method of detecting pathological cartilage turnover in a mammalian subject, preferably a human subject. The method comprises contacting a sample from the mammalian subject with at least one antibody directed to a neoepitope of mammalian COMP. The neoepitope is formed by cleavage of the mammalian COMP, preferably human COMP, at least one cleavage site selected from a group consisting of between position 77 ($S^{77}$) and position 78 ($V^{78}$); position 88 ($L^{88}$) and position 89 ($L^{89}$); position 90 ($H^{90}$) and position 91 ($C^{91}$); position 104 ($Q^{104}$) and position 105 ($T^{105}$); position 190 ($N^{190}$) and position 191 ($C^{191}$); position 194 ($N^{194}$) and position 195 ($S^{195}$); position 226 ($Q^{226}$) and position 227 ($R^{227}$); position 531 ($F^{531}$) and position 532 ($R^{532}$); position 554 ($L^{554}$) and position 555 ($N^{555}$); position 574 ($Y^{574}$) and position 575 ($T^{575}$); position 577 ($F^{577}$) and position 578 ($N^{578}$); position 657 ($T^{657}$) and position 658 ($G^{658}$); position 691 ($Q^{691}$) and position 692 ($V^{692}$), position 710 ($N^{710}$) and position 711 ($V^{711}$); and position 725 ($F^{725}$) and position 726 ($C^{726}$) of the amino acid sequence of the mammalian COMP, preferably human COMP, as defined in SEQ ID NO: 1, or any combination thereof. The method also comprises detecting, in the sample and based on the at least one antibody, presence of the neoepitope. In this method the presence of the neoepitope indicates that the mammalian subject has or is suffering from cartilage turnover.

In an embodiment, the detecting step is carried out by an immunoassay. This immunoassay is preferably multiple reaction monitoring (MRM) and/or enzyme-linked immunosorbent assay (ELISA).

In a particular embodiment, the method also comprises distinguishing between pathological cartilage turnover and benign cartilage turnover based on the at least one neoepitope as detected in the sample. Hence, if the at least one neoepitope is detected in the sample or detected at an amount or concentration exceeding a threshold value then any cartilage turnover is determined to be due to pathological cartilage turnover. Correspondingly, if no neoepitope of the embodiments is detected in the sample or detected at a significantly lower amount or concentration, i.e. below the threshold value, then any cartilage turnover is determined to be due to benign cartilage turnover.

Hence, distinguishing between pathological cartilage turnover and benign cartilage turnover comprises, in an embodiment, determining presence of pathological cartilage turnover if the amount of the at least one neoepitope detected in the sample exceeds a threshold value. Corresponding, presence of benign cartilage turnover is determined if the amount of the at least one neoepitope does not exceed the threshold value or if no such neoepitope is detected in the sample.

The threshold value used in the particular embodiment according to above can be determined by measuring the amount of the at least one neoepitope in a patient group diagnosed with a disease causing pathological cartilage turnover and optionally also measuring the amount of the at least one neoepitope in a control group with healthy subjects.

In an embodiment, the pathological cartilage turnover is caused by a disease selected from a group consisting of osteoarthritis, rheumatoid arthritis, reactive arthritis, psoriatic arthritis, juvenile chronic arthritis, a cardiovascular disease, tendon disease, osteoporosis, osteomalacia, fracture repair, arteriosclerosis, scleroderma, fibrotic skin and trauma, such as joint trauma.

The sample used in the method is preferably selected from a group consisting of a cartilage sample and a body fluid sample, such as a synovial fluid sample, a serum sample, a plasma sample and a urine sample.

In an embodiment, detecting presence of the at least one neoepitope comprises contacting the sample with an antibody according to the embodiments and further described herein. Presence of the at least one neoepitope is detected in the sample based on the antibody. In this embodiment, determining presence of the pathological cartilage turnover comprises determining presence of the pathological cartilage turnover based on the detected presence of the at least one neoepitope in the sample.

Presence of any neoepitope of the embodiments can be determined according to various techniques known in the art for detecting protein fragments. Non-limiting but preferred such techniques include detecting the at least one neoepitope in the sample by multiple reaction monitoring (MRM) or by enzyme-linked immunosorbent assay (ELISA) using an antibody that specifically binds to a neoepitope according to the embodiments.

In a particular embodiment, the method also comprises isolating the mammalian COMP from the sample. This can be performed according to various techniques, for instance as disclosed further herein. Thus, for instance affinity enrichment of COMP can be performed using an affinity column and anti-COMP antibodies.

The method further comprises, in a particular embodiment, treating the isolated COMP by a digestive enzyme prior to detecting presence of any neoepitope of the embodiments. The digestive enzyme used to treat the isolated COMP is preferably selected from a group consisting of trypsin, chymotrypsin and endoproteinase Asp-N. The digestive enzyme treats the isolated COMP to produce a sample of COMP fragments. The detection of the neoepitope is then preferably performed on the sample of COMP fragments.

Here below follows a discussion of identifying the neoepitopes in COMP according to the embodiments.

Identification of Neoepitopes in COMP

Identification of neoepitopes in COMP (SEQ ID NO: 1) has been done on both cartilage samples and synovial fluid samples as described below. Other sources of samples such as blood, serum etc. are also possible. Since an objective of the embodiments is to distinguish disease from non-disease the neoepitopes that are present in normal cartilage turnover have been omitted.

Cartilage Samples

In this example cartilage from three patient groups and one reference group has been studied:

Group 1: Patients with rheumatoid arthritis (RA) where articular cartilage tissue was obtained at the time of surgery for joint replacement (hip and knee), hereinafter called the RA patients.

Group 2: Patients with osteoarthritis (OA), where cartilage was obtained at the time of surgery for joint replacement (late stage OA), primarily hip cartilage, hereinafter called the OA patients.

Group 3: Patients that are clinically joint healthy, but as a result of cancer in the proximal part of the leg have to undergo amputation above the knee. The knee is not affected by the tumor. Some patients in the 55-75 year age range have a normal knee articular cartilage by macroscopic investigation (sometimes verified by microscopy). Some individuals in the same age range have single areas with fibrillation. In previous studies of cartilage from these joints we have shown that there are very clear changes in matrix protein synthesis and overall composition in this cartilage and that these changes are of the same character as those that characterize the late stage of OA with extensive tissue destruction and that they therefore represent early stages of the process. We have now used samples from sites in such cartilage to identify molecular changes with focus on degradation of extracellular matrix molecules.

Reference group: Normal cartilage obtained from forensic medicine cases where individuals have died for other reasons than ill health. The normal cartilages were from knee-tibia, hip-femur, shoulder-humerus, meniscus, annulus fibrosus and nucleus pulposus (age range 36-51 years) as well as trachea and rib (age 24-36 years), well below the age where OA is common. The information therefore provides information on fragments formed by the process of normal tissue turnover and retained in the tissue.

Some fragmentations, e.g. of aggrecan and the first step in collagen I and II breakdown are the same in pathology and normal turnover, but levels can be expected to be different. In this example the inventors have compared normal and pathological tissue, making it possible to deduce which unique cleavages that are a result of the pathological process.

The search of the data was focused on peptides showing amino acid sequences present in COMP, and having a cleavage typical for trypsin at either end, while the other end showed an atypical cleavage accomplished by a proteinase active in the tissue prior to extraction and reflecting the ongoing destructive process. The site not representing a tryptic cleavage is referred to as the neoepitope.

Those neoepitopes also found in the normal cartilages were excluded from further analyses since they should represent normal cartilage turnover.

Cartilage Sample Preparation

Dissection, Pulverization and Extraction:

Approximately 1×1 cm full thickness cartilage pieces were dissected from each tissue. The macroscopically normal articular cartilage samples were taken to full-depth. The same location (loaded area) of the articular cartilage was dissected for each individual. For normal controls, the following cartilage tissues from each five individuals were extracted: articular cartilage (femoral head (F), humeral head (H), and knee medial tibial condyle (K)), intervertebral disc (annulus fibrosus (AF) and nucleus pulposus (NP)) and finally meniscus (M) (36-51 years). Trachea (T) and Rib (R) cartilage samples (n=6) were obtained from different individuals (24-36 years) than those described above.

Hip articular cartilage samples from advanced osteoarthritis were obtained at joint replacement surgery and likewise samples from rheumatoid arthritis. These samples amounted to around 3-7 mg.

Clean dissected, frozen cartilage samples were pulverized in liquid nitrogen in a chilled metal tube with a mixer mill type 301 (Retsch, Haan, Germany). Visual inspections of particles formed were made in a light microscope to optimize settings (3×60 s at 25 Hz) with 30 min cooling in-between steps, resulting in some 100 mg of a homogeneous powder per tissue. The frozen samples were weighed and extracted using 15 volumes (v/w) of chaotropic extraction buffer (4 M GuHCl, 50 mM NaAc, 100 mM 6-aminocaproic acid, 5 mM benzamidine, 5 mM N-ethylmaleimide, pH 5.8) for 24 h on an orbital shaker at +4° C. Extracts were collected after centrifugation at 13200 rpm and +4° C. for 30 min.

Cartilage samples, defined by the limited lesion area, from the femoral condyle from individuals with early osteoarthritis were those showing a single fibrillated area obtained at surgical amputation due to an osteosarcoma in the upper part of the lower extremity. For extraction the tissue was sectioned on a cryostat at −20° C. into 20 µm sections that were collected in 5 ml Sterilin tubes (Bibby Sterilin Ltd, Stone, Staffs, UK) and extracted for 24 h at 4° C. with 5 ml of 4 M guanidine-HCl, 0.05 M sodium acetate, pH 5.8, also containing 10 mM EDTA, 5 mM benzamidine hydrochloride, 0.1 M 6-aminohexanoic acid, and 5 mM N-ethylmaleimide. Extracts were separated from residues by filtration over a fiberglass filter.

Quantitative Sample Preparation:

Typically, a volume of 200 µl extract was transferred into a 2 ml tube reduced by 4 mM DTT (at +56° C. for 30 min shaking) and alkylated by 16 mM IAA (room temperature for 1 h in the dark). The extracts were precipitated with ethanol (9:1) overnight at +4° C. before centrifugation (13200 rpm at +4° C. for 30 min) followed by ethanol wash for 4 h at −20° C. to remove residual GuHCl and other salts. Samples were dried in a SpeedVac and suspended in 100 µl 0.1 M triethylammonium bicarbonate pH 8.5 before digestion with 2 µg trypsin gold at +37° C. on a shaker for about 16 h. An aliquot of 50 µl was dried and used for the iTRAQ labeling.

The isobaric 4-plex iTRAQ label was used to enable mixing of up to 3 samples and a reference sample per sample set. The reference sample was a mixture of cartilage extracts originating from femoral head, rib, meniscus and nucleus pulposus in order to have as many proteins as possible represented in the relative quantification. All samples were compared to this reference sample and ratios between sample and reference were calculated. The labeling step was carried out as follows: samples were redissolved in 30 µl of 0.5 M triethylammonium bicarbonate pH 8.5. The iTRAQ reagents were brought to room temperature, redissolved in 70 µl ethanol, vortexed and centrifuged immediately before addition to the samples. Incubation was performed for 1 h at room temperature. The reaction was stopped by the addition of 100 µl water. To check the labeling efficiency an aliquot (0.5%) of the labeled sample was injected onto the iontrap LC-MS. The generated data was checked for incomplete labeling using variable iTRAQ modification in the database search. Labeled digests were dried in a SpeedVac and washed twice with 500 µl 50% acetonitrile in 0.1% formic acid for salt removal and then dried again. Labeled samples were redissolved in 100 µl 2% formic acid. The samples were mixed in a 1:1:1 ratio together with reference sample and diluted up to 500 µl with cation exchange starting buffer before injection onto the ion exchange column. Since all analyses used the same reference, all sample data could be compared by normalization against this. We selected to analyze the articular cartilages (femoral head, humeral head and knee medial tibial condyle) as one mixture (FHK) since they were expected to be most similar. The other mixture (MAN) was meniscus together with the disc structures annulus fibrosus and nucleus pulposus while the last mixture was rib and trachea in various combinations. In other sample sets the following samples were analyzed each representing one patient (early OA cartilage-1, early OA cartilage-2, early OA cartilage-3, early OA cartilage-4, early OA cartilage-5, early OA cartilage-6, late OA cartilage-7, early OA cartilage-8, RA cartilage-1, RA cartilage-2, RA cartilage-3, RA cartilage-4), RA cartilage-5, RA cartilage-6, and normal cartilage. Three samples tagged with different ITRAQ reporters were mixed with the reference sample, which was tagged with a fourth ITRAQ reporter. Using the same reference sample in all sets of analyses will allow for a quantitative comparison between all samples.

Off-Line Cation Exchange Chromatography

Initial ion exchange separations were performed on a micro-LC system (SMART, Pharmacia, Uppsala Sweden) using a strong cation exchange (SCX) column (2.1 mm i.d.×100 mm, 5 µm polysulfoethyl Aspartamide, pore size 300 Å, PolyLC, Columbia, Md., USA). Elution was isocratic for 13 min with 99.5% of solvent A (10 mM potassium phosphate, 20% acetonitrile, pH 2.8) and 0.5% solvent B (1 M KCl, 10 mM potassium phosphate, 20% acetonitrile, pH 2.8) followed by a 60 min linear gradient of increasing salt concentration to 130 mM. Subsequently the gradient increased over 15 min up to 385 mM KCl and finally for 6 min up to 1 M salt. Fractions of 300-500 µl were collected in 0.5 ml Eppendorf tubes (Safelock™, Eppendorf AG, Hamburg, Germany).

Mass Spectrometry

Fractions from the off-line SCX separation were dried, redissolved in 60 µl 0.2% formic acid whereof 10 µl were purified and concentrated using homemade reversed phase tips, 4 discs thick (Rappsilber et al., Anal. Chem. (2003), vol. 75, pp 663-670). Retained peptides were eluted using 10 µl 50% acetonitrile in 0.1% formic acid into autosampler glass vials (Qsert, Waters, Milford, Mass., USA). The organic solvent was evaporated using a SpeedVac and peptides were redissolved in 10 µl 0.2% formic acid before injection onto the various LC-MS systems. The labeling efficiency was tested by injecting a small aliquot of each sample onto an iontrap LC-MS system before mixing the samples into sample sets.

Q-TOF LC-MS

The Q-tof MS (Q-TOF micro, Waters) was connected to a CapLC (Waters) with the same type of precolumn as described above and a Waters Symmetry, C18, 3.5 µm particles, 150 mm long×75 µm i.d. analytical column. The analytical column was coupled to a Picolip™ needle (New Objective, Woburn, Mass., USA). The on-line reversed-phase separation was performed using a flow rate of about 250 nl/min and a linear gradient from 5% B (mobile phases as for the iontrap LC-MS) to 51% B in 60 min, followed by a wash for 6 min with 95% B, and reconditioning to initial conditions in 12 min. Blank runs were run as before to minimize cross contamination between fractions. The instrument was operating using data-dependent acquisition by selecting the four most intense ions as long, as they are multiply charged, for MSMS during 2 s.

Database Searching

The mass spectrometric raw data was processed using Protein Lynx 2.1 (Waters) and nano-lockspray calibration using the erythromycin peak at 716.45 Da as calibrant mass. The processed files were searched using MASCOT with the following search parameters: iTRAQ (N-term), iTRAQ (K) and carbamidomethylation (C) as fixed modifications. While mannosylation (W), iTRAQ (Y), deamidation (N, Q), oxidation (M, P) were considered as variable modifications. Other MASCOT search parameters were: monoisotopic masses, ±0.2 Da peptide mass tolerance, ±0.2 Da MSMS fragment mass tolerance, max miss cleavage of 2, ion score of interest>20, only highest ranked peptide matches and taxonomy *homo sapiens*. Semi-style cleavages only containing a site in one end expected from the enzyme used were applied in the search criteria for identification of peptides containing an endogenous (biological) cleavage occurring prior to isolation.

Data Analysis iTRAQ quantification parameters were: significant threshold $p<0.05$, weighted ratios, no normalization, minimum number of peptides of 1, minimum precursor charges of 2, at least homology of 0.05, software correction factors for each reporter was included.

Synovial Fluid Samples

Affinity Columns:

For affinity enrichments 1 mg of COMP antibody P2D3 or 0.75 mg of COMP antibody 12a11 were added to MiniLeak (KemEnTec, Denmark) gel aliquots and incubated overnight at 40) C. Unbound antibody was washed out with 0.15 M NaCl. To block unreacted sites, the gel was incubated for 3 h at room temperature with 0.2 M ethanolamine. The coupling efficiency was determined to 39% for antibody P2D3 (corresponding to 390 μg of bound antibody) and to 76% for antibody 12a11 (corresponding to 570 μg bound antibody).

Affinity Enrichment of COMP from Synovial Fluid

Synovial fluid (8 ml) from a patient diagnosed with RA (disease duration 9 months) and synovial fluid (5 ml) from a patient diagnosed with OA was incubated with 5 mM NEM (N-ethylmalemide) prior to centrifugation for 20 min 1000 g at room temperature. Synovial fluid from patient with acute trauma was diluted 2 vol with 20 mM phosphate, 150 mM NaCl, 0.8% w/v SDS and incubated for 2 h at RT. Excess of SDS was neutralized by addition of 1 vol 4% Triton-X 100 in PBS and incubated overnight at RT. The samples were first passed through a MiniLeak column without antibody to remove non-specific binding material. The non-bound sample was then applied to the P2D3 column and the flow through from the P2D3 column was directly applied to the 12a11 column. Both columns were washed with 15 ml HBS (10 mM HEPES, 150 mM NaCl, pH 7.4), followed by a wash with 2 ml of high salt buffer (10 mM HEPES, 650 mM NaCl, pH 7.4) and finally with 5 ml HBS. For elution fractions of 800 μl of 0.1 M Citrate pH 3 was added to the columns. The effluent fractions were immediately neutralized with 200 μl of 1.5 M Tris pH 8.8.

SDS-PAGE and Mass Spectrometry Sample Preparation

Prior to SDS-PAGE the eluted samples were precipitated with ethanol (9:1) overnight at +40) C. before centrifugation (13200 rpm at +4° C. for 30 min) followed by ethanol wash for 4 h at −20° C. The precipitate pellets were dissolved in SDS-PAGE sample buffer (Laemmli, Nature (1970), vol. 227, pp 680-685) without reducing agent and separated on 4-16% gradient SDS-polyacrylamide gels. Each sample was run in triplicate so that each band could be digested with three different enzymes. After staining overnight with Blue silver stain (Candiano et al., Electrophoresis (2004), vol. 25(9), pp 1327-33), bands of interest were excised and reduced with 10 mM DTT (Sigma) at 56° C. for 30 min and alkylated with 50 mM iodoacetamide (Sigma) for 30 min at room temperature. Bands were digested overnight at 37° C. with either 20 ng/μl of Trypsin (Promega) in 25 mM $NH_4HCO_3$, 50 ng/μl of Chymotrypsin (Roche) in 25 mM $NH_4HCO_3$, or 40 ng/μl of Asp-N(Roche) in 50 mM phosphate pH 8. Peptides were extracted consecutively with 1% TFA, twice with 50% acetonitrile in 0.1% TFA and with 100% acetonitrile. After drying the extracted peptides were dissolved in 10 μl 0.1% TFA and purified on C18 Stage Tips as described above.

Mass Spectrometry

Purified peptide samples were dissolved in 10 μl 0.2% formic acid and a sample (8 μl) was injected to an Esquire HCT IonTrap (Bruker Daltonik GmbH). The IonTrap was equipped with an Ultimate HPLC system (LC Packings) with a Pepmap™ nano-precolumn (LC Packings, C18, 300 μm i.d. and 5 mm long) and an Atlantis™ analytical column (Waters, C18, 3 μm particles, 150 μm i.d.×150 mm long). The analytical column was coupled to the MS instrument through a microflow nebuliser. The on-line reversed-phase separation was performed as described in the previous section. Database search settings were the same as previously described but without ITRAQ modification. Peptide and fragment mass tolerance were set to ±0.4 Da.

Semi-style cleavages only containing a site in one end expected from the enzyme used were applied in the search criteria for identification of peptides containing an endogenous (biological) cleavage occurring prior to isolation.

Results

The neoepitopes identified are listed in Table 2 below showing the cleavage sites identified in pathological COMP turnover. In Table 2, the part of the cleavage site that is represented in bold belongs to the sequence identified by MS and includes the terminal amino acid of the neoepitope (representing the position of the cleavage).

TABLE 2

Neoepitopes

| Peptide fragment identified by MS | Sample (enzyme) | Neoepitopes and Cleavage site | Cleavage position |
|---|---|---|---|
| NTVMECDACGMQQS (SEQ ID NO: 2) | SF (tryp) | GMQQS (SEQ ID NO: 18) / VRTGL (SEQ ID NO: 33) | $S^{77}/V^{78}$ |

TABLE 2-continued

Neoepitopes

| Peptide fragment identified by MS | Sample (enzyme) | Neoepitopes and Cleavage site | Cleavage position |
|---|---|---|---|
| LHCAPGFCFPGVACIQTESGAR (SEQ ID NO: 3) | cartilage (tryp) | SVRPL (SEQ ID NO: 19) / LHCAP (SEQ ID NO: 34) | $L^{88}/L^{89}$ |
| CAPGFCFPGVACIQTESGAR (SEQ ID NO: 4) | SF (tryp) | RPLLH (SEQ ID NO: 20) / CAPGF (SEQ ID NO: 35) | $H^{90}/C^{91}$ |
| TESGARCGPCPAGF (SEQ ID NO: 10) | SF (CT) | VACIQ (SEQ ID NO: 21) / TESGA (SEQ ID NO: 36) | $Q^{104}/T^{195}$ |
| CVPNSVCINTR (SEQ ID NO: 5) | cartilage (tryp) | TGQHN (SEQ ID NO: 22) / CVPNS (SEQ ID NO: 37) | $N^{190}/C^{191}$ |
| QVCTDINECETGQHNCVPN (SEQ ID NO: 6) + SVCINTRGSF (SEQ ID NO: 7) | cartilage (tryp) + SF (CT) | NCVPN (SEQ ID NO: 23) / SVCIN (SEQ ID NO: 38) | $N^{194}/S^{195}$ |
| QCGPCQPGFVGDQASGCQRRAQ (SEQ ID NO: 8) | SF (CT) | QRRAQ (SEQ ID NO: 24) / RFCPD (SEQ ID NO: 39) | $Q^{226}/R^{227}$ |
| IDVCPENAEVTLTDF (SEQ ID NO: 9) | SF (tryp) | TLTDF (SEQ ID NO: 25) / RAFQT (SEQ ID NO: 40) | $F^{531}/R^{532}$ |
| NQGREIVQTMNS (SEQ ID NO: 11) | SF (AspN) | NWVVL (SEQ ID NO: 26) / NQGRE (SEQ ID NO: 41) | $L^{554}/N^{555}$ |
| EIVQTMNSDPGLAVGY (SEQ ID NO: 12) | cartilage (tryp) + SF (tryp) | LAVGY (SEQ ID NO: 27) / TAFNG (SEQ ID NO: 42) | $Y^{574}/T^{575}$ |
| EIVQTMNSDPGLAVGYTAF (SEQ ID NO: 13) | cartilage + SF (tryp) | GYTAF (SEQ ID NO: 28) / NGVDF (SEQ ID NO: 43) | $F^{577}/N^{578}$ |
| GDTESQVRLLWK (SEQ ID NO: 14) | SF (AspN) | ALWHT (SEQ ID NO: 29) / GDTES (SEQ ID NO: 44) | $T^{657}/G^{658}$ |
| WFLQHRPQ (SEQ ID NO: 15) | cartilage (tryp) | QHRPQ (SEQ ID NO: 30) / VGYIR (SEQ ID NO: 45) | $Q^{691}/V^{692}$ |
| FYEGPELVADSN (SEQ ID NO: 16) | cartilage (tryp) | VADSN (SEQ ID NO: 31) / VVLDT (SEQ ID NO: 46) | $N^{710}/V^{711}$ |
| CFSQENIIWANLR (SEQ ID NO: 17) | cartilage (tryp) | RLGVF (SEQ ID NO: 32) / CFSQE (SEQ ID NO: 47) | $F^{725}/C^{726}$ |

The results show unique neoepitopes present in pathological cartilage turnover.

The detection or monitoring of the unique neoepitopes represents a new method for detecting pathological cartilage breakdown. This method may be used for diagnosing patients suffering from diseases including, but not limited to RA, OA, ReA, psoriatic arthritis, juvenile chronic arthritis, cardiovascular disease, tendon disease, osteoporosis, osteomalacia, fracture repair, arteriosclerosis, scleroderma, fibrotic skin or trauma, such as joint trauma. This method is especially useful in early diagnosis of such diseases.

The method disclosed herein will detect and monitor pathological cartilage and COMP turnover in disease. This is possible thanks to the identification of specific COMP neoepitopes unique for pathological cartilage breakdown.

Another aspect of the embodiments relates to an isolated C-terminally truncated fragment of mammalian COMP, preferably human COMP. According to this aspect, a C-terminal of the fragment is amino acid 77 of SEQ ID NO: 1, and the fragment comprises at least three consecutive amino acids of SEQ ID NO: 18 starting from a C-terminal of SEQ ID NO: 18 and extending towards an N-terminal of SEQ ID NO: 18;

a C-terminal of the fragment is amino acid 88 of SEQ ID NO: 1, and the fragment comprises at least three consecutive amino acids of SEQ ID NO: 19 starting from a C-terminal of SEQ ID NO: 19 and extending towards an N-terminal of SEQ ID NO: 19;
a C-terminal of the fragment is amino acid 90 of SEQ ID NO: 1, and the fragment comprises at least three consecutive amino acids of SEQ ID NO: 20 starting from a C-terminal of SEQ ID NO: 20 and extending towards an N-terminal of SEQ ID NO: 20;
a C-terminal of the fragment is amino acid 104 of SEQ ID NO: 1, and the fragment comprises at least three consecutive amino acids of SEQ ID NO: 21 starting from a C-terminal of SEQ ID NO: 21 and extending towards an N-terminal of SEQ ID NO: 21;
a C-terminal of the fragment is amino acid 190 of SEQ ID NO: 1, and the fragment comprises at least three consecutive amino acids of SEQ ID NO: 22 starting from a C-terminal of SEQ ID NO: 22 and extending towards an N-terminal of SEQ ID NO: 22;
a C-terminal of the fragment is amino acid 194 of SEQ ID NO: 1, and the fragment comprises at least three consecutive amino acids of SEQ ID NO: 23 starting from a C-terminal of SEQ ID NO: 23 and extending towards an N-terminal of SEQ ID NO: 23;
a C-terminal of the fragment is amino acid 226 of SEQ ID NO: 1, and the fragment comprises at least three consecutive amino acids of SEQ ID NO: 24 starting from a C-terminal of SEQ ID NO: 24 and extending towards an N-terminal of SEQ ID NO: 24;
a C-terminal of the fragment is amino acid 531 of SEQ ID NO: 1, and the fragment comprises at least three consecutive amino acids of SEQ ID NO: 25 starting from a C-terminal of SEQ ID NO: 25 and extending towards an N-terminal of SEQ ID NO: 25;
a C-terminal of the fragment is amino acid 554 of SEQ ID NO: 1, and the fragment comprises at least three consecutive amino acids of SEQ ID NO: 26 starting from a C-terminal of SEQ ID NO: 26 and extending towards an N-terminal of SEQ ID NO: 26;
a C-terminal of the fragment is amino acid 574 of SEQ ID NO: 1, and the fragment comprises at least three consecutive amino acids of SEQ ID NO: 27 starting from a C-terminal of SEQ ID NO: 27 and extending towards an N-terminal of SEQ ID NO: 27;
a C-terminal of the fragment is amino acid 577 of SEQ ID NO: 1, and the fragment comprises at least three consecutive amino acids of SEQ ID NO: 28 starting from a C-terminal of SEQ ID NO: 28 and extending towards an N-terminal of SEQ ID NO: 28;
a C-terminal of the fragment is amino acid 657 of SEQ ID NO: 1, and the fragment comprises at least three consecutive amino acids of SEQ ID NO: 29 starting from a C-terminal of SEQ ID NO: 29 and extending towards an N-terminal of SEQ ID NO: 29;
a C-terminal of the fragment is amino acid 691 of SEQ ID NO: 1, and the fragment comprises at least three consecutive amino acids of SEQ ID NO: 30 starting from a C-terminal of SEQ ID NO: 30 and extending towards an N-terminal of SEQ ID NO: 30;
a C-terminal of the fragment is amino acid 710 of SEQ ID NO: 1, and the fragment comprises at least three consecutive amino acids of SEQ ID NO: 31 starting from a C-terminal of SEQ ID NO: 31 and extending towards an N-terminal of SEQ ID NO: 31; or
a C-terminal of the fragment is amino acid 725 of SEQ ID NO: 1, and the fragment comprises at least three consecutive amino acids of SEQ ID NO: 32 starting from a C-terminal of SEQ ID NO: 32 and extending towards an N-terminal of SEQ ID NO: 32.

As used herein, "a fragment comprising at least three consecutive amino acids of a given amino acid sequence starting from a C-terminal of the given amino acid sequence and extending towards an N-terminal of the given amino acid sequence" implies that the fragment comprises at least the amino acid at the C-terminal of the given amino acid sequence; the amino acid prior to, in the direction towards the N-terminal of the given amino acid sequence, the C-terminal of the given amino acid sequence and the amino acid second prior to the C-terminal of the given amino acid sequence. For instance, assume that the given amino acid sequence is SEQ ID NO: 18, i.e. GMQQS. In such a case, the fragment comprises at least QQS.

In a particular embodiment, the fragment comprises at least four consecutive amino acids of the amino acid sequence in any of SEQ ID NO: 18-32 starting from the C-terminal of the any of SEQ ID NO: 18-32 (see column 4 of Table 2) and extending towards the N-terminal of the any of SEQ ID NO: 18-32.

In another particular embodiment, the fragment comprises at least five consecutive amino acids of the amino acid sequence in any of SEQ ID NO: 18-32 starting from the C-terminal of the any of SEQ ID NO: 18-32 (see column 4 of Table 2) and extending towards the N-terminal of the any of SEQ ID NO: 18-32. Hence, in this embodiment the fragment comprises the amino acid sequence in any of SEQ ID NO: 18-32. In a particular embodiment, the fragment consists of the amino acid sequences in any of SEQ ID NO: 18-32.

Other variants could be isolated C-terminally truncated fragments comprising more than five amino acids, such as six, seven, eight, nine, ten, eleven or twelve amino acids. In such a case, the C-terminally truncated fragment has a C-terminal that is amino acid 77, 88, 90, 104, 190, 194, 226, 531, 554, 574, 577, 657, 691, 710 or 725 of SEQ ID NO: 1 and has an amino acid sequence corresponding to six, seven, eight, nine, ten, eleven or twelve amino acids in SEQ ID NO: 1 starting from amino acid 77, 88, 90, 104, 190, 194, 226, 531, 554, 574, 577, 657, 691, 710 or 725 of SEQ ID NO: 1 and extending towards the N-terminal of SEQ ID NO: 1.

In a particular embodiment, the isolated C-terminally truncated fragment has an amino sequence as defined in any of SEQ ID NO: 2, 6, 8, 9, 12, 13, 15, 16, 18-32, preferably as defined in any of SEQ ID NO: 18-32.

Another aspect of the embodiments relates to an isolated N-terminally truncated fragment of mammalian COMP, preferably human COMP. According to this aspect,
an N-terminal of the fragment is amino acid 78 of SEQ ID NO: 1, and the fragment comprises at least three consecutive amino acids of SEQ ID NO: 33 starting from an N-terminal of SEQ ID NO: 33 and extending towards a C-terminal of SEQ ID NO: 33;
an N-terminal of the fragment is amino acid 89 of SEQ ID NO: 1, and the fragment comprises at least three consecutive amino acids of SEQ ID NO: 34 starting from an N-terminal of SEQ ID NO: 34 and extending towards a C-terminal of SEQ ID NO: 34;
an N-terminal of the fragment is amino acid 91 of SEQ ID NO: 1, and the fragment comprises at least three consecutive amino acids of SEQ ID NO: 35 starting from an N-terminal of SEQ ID NO: 35 and extending towards a C-terminal of SEQ ID NO: 35;
an N-terminal of the fragment is amino acid 105 of SEQ ID NO: 1, and the fragment comprises at least three consecutive amino acids of SEQ ID NO: 36 starting from an N-terminal of SEQ ID NO: 36 and extending towards a C-terminal of SEQ ID NO: 36;

an N-terminal of the fragment is amino acid 191 of SEQ ID NO: 1, and the fragment comprises at least three consecutive amino acids of SEQ ID NO: 37 starting from an N-terminal of SEQ ID NO: 37 and extending towards a C-terminal of SEQ ID NO: 37;

an N-terminal of the fragment is amino acid 195 of SEQ ID NO: 1, and the fragment comprises at least three consecutive amino acids of SEQ ID NO: 38 starting from an N-terminal of SEQ ID NO: 38 and extending towards a C-terminal of SEQ ID NO: 38;

an N-terminal of the fragment is amino acid 227 of SEQ ID NO: 1, and the fragment comprises at least three consecutive amino acids of SEQ ID NO: 39 starting from an N-terminal of SEQ ID NO: 39 and extending towards a C-terminal of SEQ ID NO: 39;

an N-terminal of the fragment is amino acid 532 of SEQ ID NO: 1, and the fragment comprises at least three consecutive amino acids of SEQ ID NO: 40 starting from an N-terminal of SEQ ID NO: 40 and extending towards a C-terminal of SEQ ID NO: 40;

an N-terminal of the fragment is amino acid 555 of SEQ ID NO: 1, and the fragment comprises at least three consecutive amino acids of SEQ ID NO: 41 starting from an N-terminal of SEQ ID NO: 41 and extending towards a C-terminal of SEQ ID NO: 41;

an N-terminal of the fragment is amino acid 575 of SEQ ID NO: 1, and the fragment comprises at least three consecutive amino acids of SEQ ID NO: 42 starting from an N-terminal of SEQ ID NO: 42 and extending towards a C-terminal of SEQ ID NO: 42;

an N-terminal of the fragment is amino acid 578 of SEQ ID NO: 1, and the fragment comprises at least three consecutive amino acids of SEQ ID NO: 43 starting from an N-terminal of SEQ ID NO: 43 and extending towards a C-terminal of SEQ ID NO: 43;

an N-terminal of the fragment is amino acid 658 of SEQ ID NO: 1, and the fragment comprises at least three consecutive amino acids of SEQ ID NO: 44 starting from an N-terminal of SEQ ID NO: 44 and extending towards a C-terminal of SEQ ID NO: 44;

an N-terminal of the fragment is amino acid 692 of SEQ ID NO: 1, and the fragment comprises at least three consecutive amino acids of SEQ ID NO: 45 starting from an N-terminal of SEQ ID NO: 45 and extending towards a C-terminal of SEQ ID NO: 45;

an N-terminal of the fragment is amino acid 711 of SEQ ID NO: 1, and the fragment comprises at least three consecutive amino acids of SEQ ID NO: 46 starting from an N-terminal of SEQ ID NO: 46 and extending towards a C-terminal of SEQ ID NO: 46; or an N-terminal of the fragment is amino acid 726 of SEQ ID NO: 1, and the fragment comprises at least three consecutive amino acids of SEQ ID NO: 47 starting from an N-terminal of SEQ ID NO: 47 and extending towards a C-terminal of SEQ ID NO: 47.

As used herein, "a fragment comprising at least three consecutive amino acids of a given amino acid sequence starting from an N-terminal of the given amino acid sequence and extending towards a C-terminal of the given amino acid sequence" implies that the fragment comprises at least the amino acid at the N-terminal of the given amino acid sequence; the amino acid following, in the direction towards the C-terminal of the given amino acid sequence, the N-terminal of the given amino acid sequence and the second amino acid following the N-terminal of the given amino acid sequence. For instance, assume that the given amino acid sequence is SEQ ID NO: 33, i.e. VRTGL. In such a case, the fragment comprises at least VRT.

In a particular embodiment, the fragment comprises at least four consecutive amino acids of the amino acid sequence in any of SEQ ID NO: 33-47 starting from the N-terminal of the any of SEQ ID NO: 33-47 (see column 4 of Table 2) and extending towards the C-terminal of the any of SEQ ID NO: 33-47.

In another particular embodiment, the fragment comprises at least five consecutive amino acids of the amino acid sequence in any of SEQ ID NO: 33-47 starting from the N-terminal of the any of SEQ ID NO: 33-47 (see column 4 of Table 2) and extending towards the C-terminal of the any of SEQ ID NO: 33-47. Hence, in this embodiment the fragment comprises the amino acid sequences in any of SEQ ID NO: 33-47. In a particular embodiment, the fragment consists of the amino acid sequences in any of SEQ ID NO: 33-47.

Other variants could be isolated N-terminally truncated fragments comprising more than five amino acids, such as six, seven, eight, nine, ten, eleven or twelve amino acids. In such a case, the N-terminally truncated fragment has an N-terminal that is amino acid 78, 89, 91, 105, 191, 195, 227, 532, 555, 575, 578, 658, 692, 711 or 726 of SEQ ID NO: 1 and has an amino acid sequence corresponding to six, seven, eight, nine, ten, eleven or twelve amino acids in SEQ ID NO: 1 starting from amino acid 78, 89, 91, 105, 191, 195, 227, 532, 555, 575, 578, 658, 692, 711 or 726 of SEQ ID NO: 1 and extending towards the C-terminal of SEQ ID NO: 1.

In a particular embodiment, the isolated N-terminally truncated fragment has an amino sequence as defined in any of SEQ ID NO: 3-5, 7, 10, 11, 14, 17, 33-47, preferably as defined in any of SEQ ID NO: 33-47.

Longer fragments may also be used, as long as the terminal amino acid is identical with the terminal amino acid of the peptides in Table 2 (represented by the amino acid under "position" in Table 2).

Peptides are sometimes not antigenic on their own. Therefore peptides are often coupled to a foreign protein or peptide carrier thereby acting as a hapten. Usually, such peptide carriers are chosen such that they do not occur in any species to be investigated to avoid reaction of the antibodies to this peptide carrier. In this way, reactivity will be restricted to the neoepitope on the short peptide.

A further aspect of the embodiments relates to a conjugate configured to be used for production of antibodies against at least one neoepitope of mammalian COMP, preferably human COMP. The at least one neoepitope is formed by cleavage of the mammalian COMP at least one cleavage site selected from a group consisting of between position 77 ($S^{77}$) and position 78 ($V^{78}$); position 88 ($L^{88}$) and position 89 ($L^{89}$); position 90 ($H^{90}$) and position 91 ($C^{91}$); position 104 ($Q^{104}$) and position 105 ($T^{105}$); position 190 ($N^{190}$) and position 191 ($C^{191}$); position 194 ($N^{194}$) and position 195 ($S^{195}$); position 226 ($Q^{226}$) and position 227 ($R^{227}$); position 531 ($F^{531}$) and position 532 ($R^{532}$); position 554 ($L^{554}$) and position 555 ($N^{555}$); position 574 ($Y^{574}$) and position 575 ($T^{575}$); position 577 ($F^{577}$) and position 578 ($N^{578}$); position 657 ($T^{657}$) and position 658 ($G^{658}$); position 691 ($Q^{691}$) and position 692 ($V^{692}$), position 710 ($N^{710}$) and position 711 ($V^{711}$); and position 725 ($F^{725}$) and position 726 ($C^{726}$) of the amino acid sequence of said mammalian COMP as defined in SEQ ID NO: 1, or a combination thereof. The conjugate comprises at least one isolated C-terminally truncated fragment according to above and/or at least one isolated N-terminally truncated fragment according to above coupled to or admixed with a peptide carrier.

In an embodiment, the at least one isolated C-terminally truncated fragment is coupled to the peptide carrier via its N-terminal and the at least one isolated N-terminally truncated fragment is coupled to the peptide carrier via its C-terminal.

In a particular embodiment, the peptide carrier is selected from the group consisting of keyhole limpet hemocyanin (KLH) and ovalbumin.

The peptide carrier may also be used without covalent coupling to the peptide or fragment, i.e. provided admixed with the fragment.

The preparation of the isolated C-terminally truncated and/or N-terminally truncated fragment in vitro can be performed by a method for expressing the fragment using a recombinant DNA expression vector comprising a polynucleotide sequence encoding the fragment to be expressed. A compatible procaryotic or eucaryotic host cell is then transformed with the expression vector such that the fragment can be expressed by the host cell. The transformed host cell is cultured in a suitable growth medium to produce the fragment.

Further aspects of the embodiments relate to an isolated polynucleotide sequence encoding an isolated C-terminally truncated fragment according to above and/or an isolated N-terminally truncated fragment according to above, a recombinant expression vector comprising such an isolated polynucleotide sequence and a host cell transformed with such a recombinant expression vector.

A further aspect of the embodiments relates to the use of an isolated C-terminally truncated fragment according to above, an isolated N-terminally truncated fragment according to above and/or a conjugate according to above for production of antibodies that specifically bind to at least one neoepitope formed by cleavage of mammalian COMP at least one cleavage site selected from a group consisting of between position 77 ($S^{77}$) and position 78 ($V^{78}$); position 88 ($L^{88}$) and position 89 ($L^{89}$); position 90 ($H^{90}$) and position 91 ($C^{91}$); position 104 ($Q^{104}$) and position 105 ($T^{105}$); position 190 ($N^{190}$) and position 191 ($C^{191}$); position 194 ($N^{194}$) and position 195 ($S^{195}$); position 226 ($Q^{226}$) and position 227 ($R^{227}$); position 531 ($F^{531}$) and position 532 ($R^{532}$); position 554 ($L^{554}$) and position 555 ($N^{555}$); position 574 ($Y^{574}$) and position 575 ($T^{575}$); position 577 ($F^{577}$) and position 578 ($N^{578}$); position 657 ($T^{657}$) and position 658 ($G^{658}$); position 691 ($Q^{691}$) and position 692 ($V^{692}$), position 710 ($N^{710}$) and position 711 ($V^{711}$); and position 725 ($F^{725}$) and position 726 ($C^{726}$) of the amino acid sequence of the mammalian COMP as defined in SEQ ID NO: 1, or a combination thereof.

A related aspect of the embodiments relates to a method for production of antibodies that specifically bind to at least one neoepitope formed by cleavage of mammalian COMP at least one cleavage site selected from a group consisting of between position 77 ($S^{77}$) and position 78 ($V^{78}$); position 88 ($L^{88}$) and position 89 ($L^{89}$); position 90 ($H^{90}$) and position 91 ($C^{91}$); position 104 ($Q^{104}$) and position 105 ($T^{105}$); position 190 ($N^{140}$) and position 191 ($C^{191}$); position 194 ($N^{194}$) and position 195 ($S^{195}$); position 226 ($Q^{226}$) and position 227 ($R^{227}$); position 531 ($F^{531}$) and position 532 ($R^{532}$); position 554 ($L^{554}$) and position 555 ($N^{555}$); position 574 ($Y^{574}$) and position 575 ($T^{575}$); position 577 ($F^{577}$) and position 578 ($N^{578}$); position 657 ($T^{657}$) and position 658 ($G^{658}$); position 691 ($Q^{691}$) and position 692 ($V^{692}$), position 710 ($N^{710}$) and position 711 ($V^{711}$); and position 725 ($F^{725}$) and position 726 ($C^{726}$) of the amino acid sequence of the mammalian COMP as defined in SEQ ID NO: 1, or a combination thereof. The method comprises raising antibodies against an isolated C-terminally truncated fragment according to above, an isolated N-terminally truncated fragment according to above and/or a conjugate according to above and isolating the antibodies.

Another related aspect of the embodiments relates to an isolated antibody against an isolated C-terminally truncated fragment according to above, an isolated N-terminally truncated fragment according to above and/or a conjugate according to above. The isolated antibody specifically binds to at least one neoepitope formed by cleavage of mammalian COMP at least one cleavage site selected from a group consisting of between position 77 ($S^{77}$) and position 78 ($V^{78}$); position 88 ($L^{88}$) and position 89 ($L^{89}$); position 90 ($H^{90}$) and position 91 ($C^{91}$); position 104 ($Q^{104}$) and position 105 ($T^{105}$); position 190 ($N^{190}$) and position 191 ($C^{191}$); position 194 ($N^{194}$) and position 195 ($S^{195}$); position 226 ($Q^{226}$) and position 227 ($R^{227}$); position 531 ($F^{531}$) and position 532 ($R^{532}$); position 554 ($L^{554}$) and position 555 ($N^{555}$); position 574 ($Y^{574}$) and position 575 ($T^{575}$); position 577 ($F^{577}$) and position 578 ($N^{578}$); position 657 ($T^{657}$) and position 658 ($G^{658}$); position 691 ($Q^{691}$) and position 692 ($V^{692}$), position 710 ($N^{710}$) and position 711 ($V^{711}$); and position 725 ($F^{725}$) and position 726 ($C^{726}$) of the amino acid sequence of the mammalian COMP as defined in SEQ ID NO: 1, or a combination thereof.

A further related aspect of the embodiments defines an isolated antibody according to above for use in determining pathological cartilage turnover.

The antibodies against fragments or conjugate may be obtained by immunizing an animal with one or more fragments, one or more peptides and/or one or more conjugates according to the embodiments. The immunized animal may be selected from the group comprising humans, mice, rats, rabbits, sheep, non-human primates, goat, horse and poultry.

The antibodies according to the embodiments may also be obtained by in vitro immunization methods using one or more fragments, one or more peptides and/or one or more conjugates according to the embodiments.

The antibody according to the invention may be a polyclonal antibody or a monoclonal antibody.

Production of an antibody according to the invention may involve the phage-display approach. When generating the antibody by the phage-display approach, the antibody may be a ligand, one or more fragments of an antibody, such as a Fab (Fragment Antigen Binding) fragment or a F(ab)'2 fragment (a fragment containing two Fab), or an intact antibody.

The antibodies according to the invention may be used for the detection of neoepitopes of the embodiments, and accordingly can be used for detecting such neoepitopes in a sample, for instance, for the purpose of determining whether a mammalian subject has or is suffering from pathological cartilage turnover.

Still another aspect of the embodiments relates to a method for detecting presence of an isolated C-terminally truncated fragment of mammalian COMP according to above, an isolated N-terminally truncated fragment of mammalian COMP according to above, a conjugate according to above, or any combination thereof, in a sample. The method comprises contacting the sample with a suitable reagent which selectively interacts with the isolated C-terminally truncated fragment of mammalian COMP, the isolated N-terminally truncated fragment of mammalian COMP, and/or the conjugate under conditions in which the reagent will selectively interact with the isolated C-terminally truncated fragment of mammalian COMP, the isolated N-terminally truncated fragment of mammalian COMP, and/or the conjugate. The method also comprises detecting the interaction of the reagent with the isolated C-terminally truncated fragment of mammalian COMP, the isolated N-terminally truncated fragment of mammalian COMP, and/or the conjugate, thereby detecting the isolated C-terminally truncated fragment of mammalian COMP, the isolated N-terminally truncated fragment of mammalian COMP, and/or the conjugate in the sample.

In an embodiment, the reagent, which selectively interacts with the isolated C-terminally truncated fragment of mammalian COMP, the isolated N-terminally truncated fragment of mammalian COMP, and/or the conjugate, is an antibody, or fragment thereof, that specifically binds to the isolated C-terminally truncated fragment of mammalian COMP, the isolated N-terminally truncated fragment of mammalian COMP, and/or the conjugate.

A further aspect relates to a method for detecting the presence of an isolated C-terminally truncated fragment of mammalian COMP according to above, an isolated N-terminally truncated fragment of mammalian COMP according to above, and/or a conjugate according to above, in a sample from a mammalian subject, preferably a human subject. The method comprises contacting the sample with an antibody, or fragment thereof, that specifically binds to the isolated C-terminally truncated fragment of mammalian COMP, the isolated N-terminally truncated fragment of mammalian COMP, and/or the conjugate. The method also comprises detecting a complex between the antibody, or fragment thereof, and the isolated C-terminally truncated fragment of mammalian COMP, the isolated N-terminally truncated fragment of mammalian COMP, and/or the conjugate, thereby detecting the isolated C-terminally truncated fragment of mammalian COMP, the isolated N-terminally truncated fragment of mammalian COMP, and/or the conjugate in the sample.

In an embodiment, the sample is a cartilage sample, a body fluid sample, or any combination thereof. In a particular embodiment, the body fluid sample is a synovial fluid sample, a serum sample, a plasma sample, a urine sample, or any combination thereof.

In an embodiment, the sample is from a subject suspected of having pathological cartilage turnover.

In an embodiment, detecting the presence of the isolated C-terminally truncated fragment of mammalian COMP, the isolated N-terminally truncated fragment of mammalian COMP, and or the conjugate in the sample diagnoses the subject as having pathological cartilage turnover.

EXAMPLE 1

Peptides represented in Table 2 and representing the neoepitopes generated by pathological cleavage of COMP (SEQ ID NO: 1), were synthesized and used to immunize rabbits according to a standard protocol. Peptides were synthesized containing the 5 terminal amino acids as indicated in Table 2 (column 3), with the very terminal and non-substituted amino acid freed by cleavage indicated by its number in the sequence and with a sequence of three glycine residues followed by a cysteine in the opposite end.

The peptides were linked to Keyhole Limpet Hemocyanin via their terminal cysteine and used to immunize rabbits by standard protocols. Peptide synthesis and production of antibodies are custom services provided by Genscript Ltd (Hong Kong) using standard methods.

Titers of antibodies produced were evaluated by solid phase assay. Peptides with the terminal amino acid corresponding to the cleavage and including the neighboring 7 amino acids of the proteins natural sequence were used to coat polystyrene microtiter plates (Nunc, Maxisorp) at 1 µg/ml in PBS-buffer. The antisera were added to the respective coated peptides at variable dilutions (from 1:200 in steps of 5 to 1:25000) and bound antibodies were detected by a swine anti-rabbit alkaline phosphatase conjugated antibody according to standard methods as known in the art.

Titer curves are provided in FIG. 1.

EXAMPLE 2

Synovial fluid was collected by joint aspiration and immediately centrifuged to remove cells and any particles. The synovial fluid was diluted 1:10 in sample diluent as the serum samples.

Competition ELISA assays were developed for a neoepitope and were applied to quantify the respective COMP-fragment in synovial fluid samples from patients with RA or OA and for control blood samples from healthy donors.

96-well microtiter plates (Nunc-Immunoplates, Maxisorp, Nunc Intermed Ltd, Copenhagen, Denmark) were coated overnight at room temperature in a wet chamber with 50 µl of the 8-amino acid COMP peptide CEVTLTDF$^{531}$ at 25 ng/ml in PBS pH 7. After rinsing the plates with 0.15 M sodium chloride and 0.05% (w/v) Tween 20 the free binding sites of the polystyrene surface were blocked with 120 µl of 2 mg/ml bovine serum albumin (Sigma-Aldrich) in PBS, pH 7.5 for 1 h at room temperature.

Figure 2:
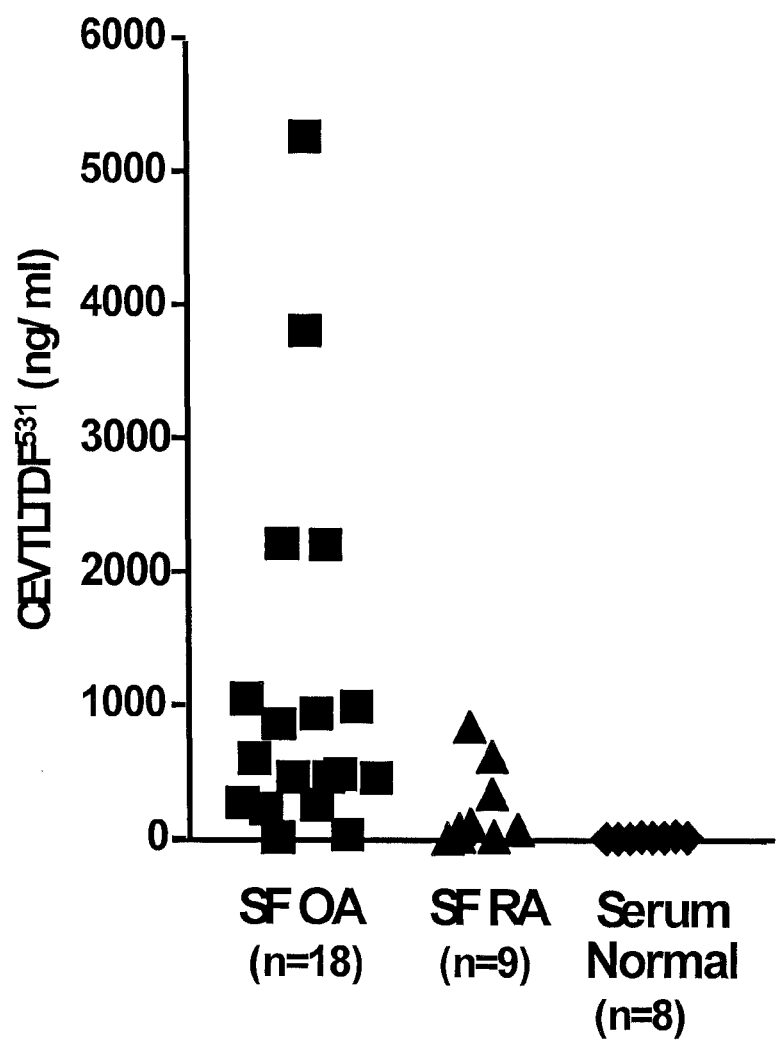
FIG. 2 shows the results from an assay for COMP fragments released into synovial fluid containing a cleavage neoepitope.

The COMP peptide CEVTLTDF was used as standard to generate a calibration curve. The standard was diluted (from 0.244 to 250 ng/ml) in a solution of 0.5% BSA, 0.8% (w/v) SDS, 10 mM EDTA in 0.1 M sodium chloride, 0.05 M sodium phosphate pH 7.5. Samples of synovial fluids and sera were diluted 10 times in 0.8% (w/v) SDS, 10 mM EDTA, 0.1 M sodium chloride, 0.05 M sodium phosphate pH 7.5. Thirty microliters of the diluted standard and samples were incubated in a sterilin plate (Bibby Sterilin Ltd., U.K.) overnight at room temperature in a wet chamber. Next day to the sterilin plate were added 30 µl of diluted antibodies (1:15000 anti-CEVTLTDF) in 4% Triton in 10 mM phosphate ($NaH_2PO_4$) pH 7.5. After 1 h pre-incubation at room temperature 50 µl of the mixture was added to the coated wells of the NUNC plate. After 1 h incubation at room temperature the plates were rinsed as above and the bound antibodies were detected by adding 50 µl of a 1:1000 dilution of swine-anti-rabbit IgG conjugated with alkaline phosphatase (DAKO A/S, Denmark) in 2 mg/ml of bovine serum albumin, 0.1 M sodium chloride, 0.05 M sodium phosphate pH 7.5. After 1 h incubation at room temperature the plates were rinsed as above and 100 µl of substrate was added (1 mg/ml p-nitrophenyl phosphate in 1 M diethanolamine pH 9.8 containing 0.5 M $MgCl_2$). The absorbance of each sample and standard was measured at 405 nm in duplicate by a microplate reader (Expert96, AsysHitech, Austria). The Mikrowin 200 software program (AsysHitech, Austria) was used to plot the calibration curve and to calculate the content of COMP neoepitopes in the samples analyzed. The measured levels of COMP-fragments in synovial fluids from RA and OA respectively are shown in FIG. 2.

EXAMPLE 3

Figure 3:
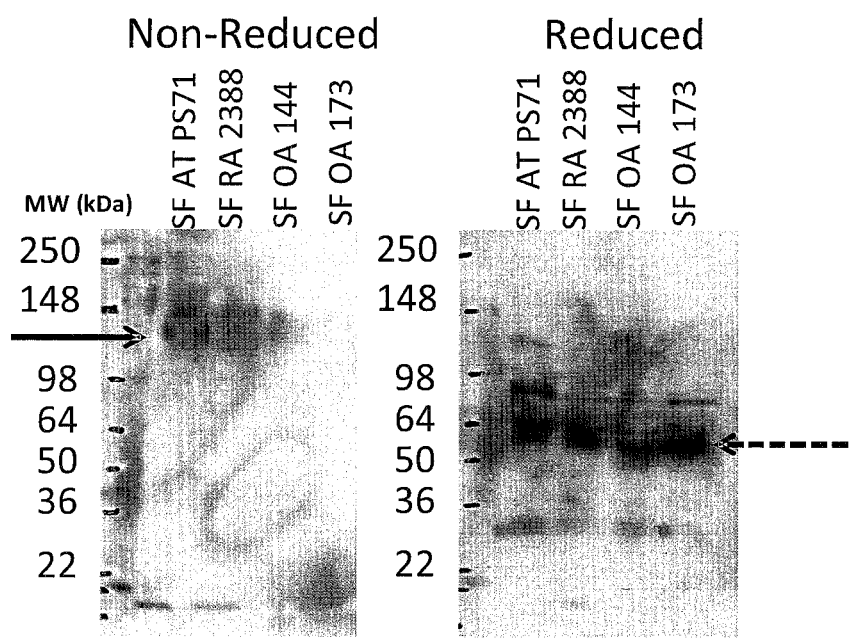
FIG. 3 shows an analysis by western blot of synovial fluid samples precipitated with PEG 6000 using a neoepitope antibody for detection.

Synovial fluid samples (50 µl) were diluted with one volume of 100 mM sodium phosphate pH 7.5, 20 mM EDTA and 1 M NaCl. To the diluted synovial fluid was added 35

µl of 50% (w/v) Polyethylene-glycol 6000 (Merck KGaA, Germany) in 50 mM sodium phosphate pH 7.5, 10 mM EDTA and 0.5 M NaCl. The mixture was incubated for 60 min at room temperature and then centrifuged at 12000 g for 15 minutes at 4° C. The collected pellet was resuspended in 200 µl of 20 mM Tris, 150 mM NaCl pH 7.4 and transferred to a tube containing 75 µl of Protein A sepharose. The mixture was incubated for 15 minutes and the tubes were centrifuged at 300 g for 2 minutes. The supernatant was collected and precipitated with 9 volumes of 95% ethanol. Precipitated proteins were dissolved in electrophoresis sample buffer (2% SDS, 0.125 M Tris-HCl, pH 6.8, 0.002% Bromphenol blue and 20% Glycerol) without or with 10% of 2-mercaptoethanol for reduction, boiled at 100° C. for 4 min and separated on gradient polyacrylamide (4-16%) slab gels with a 4% stacking gel. The separated proteins were transfer to Nitrocellulose membrane (Millipore). For immunoblotting the membranes were blocked in 3% bovine serum albumin in Tris buffered saline pH 7.2 containing 0.05% Tween 20 overnight at 4° C. and then incubated for 1 h at room temperature with the antibodies diluted 1:2000 in 3% bovine serum albumin in Tris buffered saline pH 7.2. Following three washes with Tris buffered saline pH 7.2 containing 0.05 Tween 20 was added anti-rabbit IgG horseradish peroxidase secondary antibody (Jackson Laboratories, USA) diluted 1:25000 in the same solution as the primary antibody and incubated for 1 h at room temperature. Following washing, the signal was developed with ECL Western blotting detection system (Thermo Scientific) and detected using Agfa Cronex 5 film. The western blots with one of the neoepitope antibodies are shown in FIG. 3.

EXAMPLE 4

Figure 4:
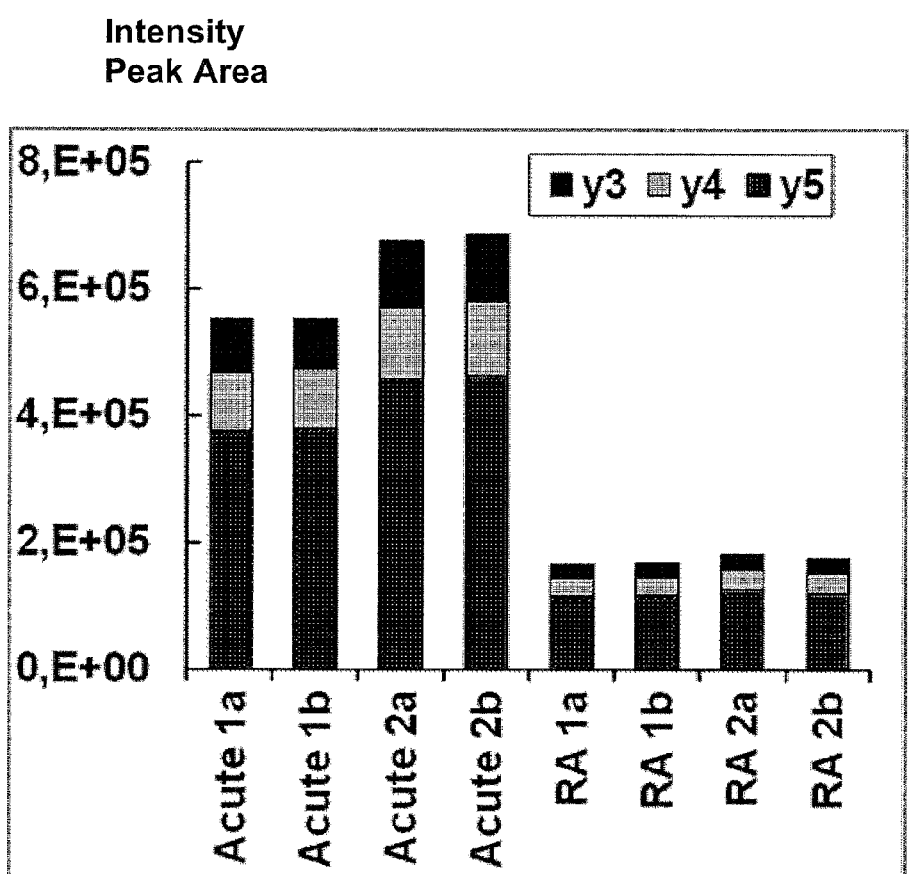
FIG. 4 shows the detection of a neoepitope using MRM analysis of synovial fluid precipitated with PEG 6000.

Synovial fluid samples were prepared as described in Example 3 but after the Protein A sepharose step there was a rd precipitation step with 12.5% PEG 6000 to reduce the sample volume. The pellet was resuspended in Tris buffer saline pH 7.2 to the original volume of synovial fluid. An aliquot of the sample was reduced (10 mM dithiothreitol, DTT) and alkylated (50 mM iodoacetamide, IAA) before digestion overnight at 37° C. with trypsin (Promega). The trypsinated samples were filtered through a 30 kDa spin filter (Nanosep 30 k, PALL life sciences) followed by a $C_{18}$ spin filter (SS18V, Nest Group, Inc., USA) for desalting. An injection volume corresponding to 1.25 µl synovial fluid sample was injected onto the triple quadrupole mass spectrometer (TSQ Vantage, Thermo Scientific, USA) and multiple reaction monitoring (MRM) experiments were performed for the neo-epitope peptide ($S^{195}$VCINTR). The fragment ions y4, y5 and y6 were measured from the peptide precursor (425.22, 2+). The sum of these fragment signals (transitions) are shown in FIG. 4 were double injections (a, b) were made for two acute trauma and two rheumatoid arthritis samples, respectively. The acute trauma samples contained higher levels of the neoepitope than the RA samples but it was still detected in all the samples tested. It should be noted that the samples in this example are different than the sample for the discovery of the neoepitope. In addition, the complementary side of the actual cleavage site was detected in tissue samples from early OA tissue (group 3 as described before).

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A method of determining pathological cartilage turnover in a patient, comprising;

mammalian obtaining a cartilage sample or a body fluid sample from the patient, conducting an immunoassay to measure fragments of mammalian Cartilage Oligomeric Matrix Protein, COMP, having an N- or C-terminal neo epitope formed by cleavage of COMP by a proteinase, said fragments being naturally present in said sample, and associating an elevation of said measure in said patient above a normal level with the presence or extent of pathological cartilage turnover, wherein said immunoassay is conducted by a method comprising:

contacting the fragments of COMP having said N- or C-terminal neo epitope that are naturally present in said sample with an isolated antibody that specifically binds to the N- or C-terminal neo-epitope, and measuring an extent of binding of the N- or C-terminal neo-epitope to said isolated antibody to measure therein fragments comprising said neo-epitope, wherein said isolated antibody specifically binds to an N-terminal neo-epitope selected from the group consisting of:

VRTGL . . . (SEQ ID NO 33)

LHCAP . . . (SEQ ID NO 34)

CAPGF . . . (SEQ ID NO 35)

TESGA . . . (SEQ ID NO 36)

CVPNS . . . (SEQ ID NO 37)

SVCIN . . . (SEQ ID NO 38)

RFCPD . . . (SEQ ID NO 39)

RAFQT . . . (SEQ ID NO 40)

NOGRE . . . (SEQ ID NO 41)

TAFNG . . . (SEQ ID NO 42)

NGVDF . . . (SEQ ID NO 43)

GDTES . . . (SEQ ID NO 44)

VGYIR . . . (SEQ ID NO 45)

VVLDT . . . (SEQ ID NO 46)

CFSQE . . . (SEQ ID NO 47)

or wherein said isolated antibody specifically binds to a C-terminal neo-epitope selected from the group consisting of:

. . . GMQQS (SEQ ID NO 18)

. . . SVRPL (SEQ ID NO 19)

. . . RPLLH (SEQ ID NO 20)

. . . VACIQ (SEQ ID NO 21)

. . . TGQHN (SEQ ID NO 22)

. . . NCVPN (SEQ ID NO 23)

. . . QRRAQ (SEQ ID NO 24)

. . . TLTDF (SEQ ID NO 25)

. . . NWVVL (SEQ ID NO 26)

. . . LAVGY (SEQ ID NO 27)

. . . GYTAF (SEQ ID NO 28)

. . . ALWHT (SEQ ID NO 29)

. . . QHRPQ (SEQ ID NO 30)

. . . VADSN (SEQ ID NO 31)

. . . RLGVF (SEQ ID NO 32)

wherein binding of the N- or C-terminal neo-epitope to the isolated antibody is a determination that pathological cartilage turnover is present in the patient.

2. The method according to claim 1, wherein said pathological cartilage turnover is caused by a disease selected from a group consisting of osteoarthritis, rheumatoid arthritis, reactive arthritis, psoriatic arthritis, juvenile chronic arthritis, a cardiovascular disease, tendon disease, osteoporosis, osteomalacia, fracture repair, arteriosclerosis, scleroderma, fibrotic skin, and joint trauma.

3. The method according to claim 1, wherein said body fluid sample is selected from a group consisting of a synovial fluid sample, a serum sample, a plasma sample and a urine sample.

4. The method according to claim 1, wherein said immunoassay is a multiple reaction monitoring assay, MRM.

5. The method according to claim 1, wherein said immunoassay is an enzyme-linked immunosorbent assay, ELISA.

6. A method for production of antibodies that specifically bind to fragments of mammalian cartilage oligomeric matrix protein, COMP, comprising an N- or C-terminal neoepitope formed by cleavage of mammalian COMP by a proteinase, said method comprising:

raising antibodies against a peptide corresponding to an N- or C-terminal neoepitope formed by cleavage of mammalian COMP and isolating said antibodies, wherein said neoepitope is an N-terminal neo-epitope selected from the group consisting of:

```
                          (SEQ ID NO 33)
      VRTGL . . .

(SEQ ID NO 34)
      LHCAP . . .

(SEQ ID NO 35)
      CAPGF . . .

(SEQ ID NO 36)
      TESGA . . .

(SEQ ID NO 38)
      SVCIN . . .

(SEQ ID NO 39)
      RFCPD . . .

(SEQ ID NO 40)
      RAFQT . . .

(SEQ ID NO 41)
      NQGRE . . .

(SEQ ID NO 42)
      TAFNG . . .

(SEQ ID NO 43)
      NGVDF . . .

(SEQ ID NO 44)
      GDTES . . .

(SEQ ID NO 45)
      VGYIR . . .

(SEQ ID NO 46)
      VVLDT . . .

(SEQ ID NO 47)
      CFSQE . . .
``` or wherein said neoepitope is a C-terminal neo-epitope selected from the group consisting of:

```
                          (SEQ ID NO 18)
      GMQQS (SEQ ID NO 19)
      SVRPL
```

-continued

```
                          (SEQ ID NO 20)
      RPLLH (SEQ ID NO 21)
      VACIQ (SEQ ID NO 22)
      TGQHN (SEQ ID NO 23)
      NCVPN (SEQ ID NO 24)
      QRRAQ (SEQ ID NO 25)
      TLTDF (SEQ ID NO 26)
      NWVVL (SEQ ID NO 27)
      LAVGY (SEQ ID NO 28)
      GYTAF (SEQ ID NO 29)
      ALWHT (SEQ ID NO 30)
      QHRPQ (SEQ ID NO 31)
      VADSN (SEQ ID NO 32)
      RLGVF.
```

7. An isolated antibody, wherein said isolated antibody specifically binds to an N-terminal neo-epitope selected from the group consisting of:

```
                          (SEQ ID NO 33)
      VRTGL . . .

(SEQ ID NO 34)
      LHCAP . . .

(SEQ ID NO 35)
      CAPGF . . .

(SEQ ID NO 36)
      TESGA . . .

(SEQ ID NO 38)
      SVCIN . . .

(SEQ ID NO 39)
      RFCPD . . .

(SEQ ID NO 40)
      RAFQT . . .

(SEQ ID NO 41)
      NQGRE . . .

(SEQ ID NO 42)
      TAFNG . . .

(SEQ ID NO 43)
      NGVDF . . .

(SEQ ID NO 44)
      GDTES . . .

(SEQ ID NO 45)
      VGYIR . . .
```

```
                        (SEQ ID NO 46)
VVLDT . . .

(SEQ ID NO 47)
CFSQE . . .
``` or wherein said isolated antibody specifically binds to a C-terminal neo-epitope selected from the group consisting of:

```
                        (SEQ ID NO 18)
GMQQS (SEQ ID NO 19)
SVRPL (SEQ ID NO 20)
RPLLH (SEQ ID NO 21)
VACIQ (SEQ ID NO 22)
TGQHN (SEQ ID NO 23)
NCVPN (SEQ ID NO 24)
QRRAQ (SEQ ID NO 25)
TLTDF (SEQ ID NO 26)
NWVVL (SEQ ID NO 27)
LAVGY (SEQ ID NO 28)
GYTAF (SEQ ID NO 29)
ALWHT (SEQ ID NO 30)
QHRPQ (SEQ ID NO 31)
VADSN (SEQ ID NO 32)
RLGVF.
```

8. The isolated antibody according to claim 7 for use in determining pathological cartilage turnover.

* * * * *

SEQUENCE LISTING

```
<160> NUMBER OF SEQ ID NOS: 47

<210> SEQ ID NO 1
<211> LENGTH: 757
<212> TYPE: PRT
<213> ORGANISM: Homo sapiens

<400> SEQUENCE: 1

Met Val Pro Asp Thr Ala Cys Val Leu Leu Leu Thr Leu Ala Ala Leu
1               5                   10                  15

Gly Ala Ser Gly Gln Gly Gln Ser Pro Leu Gly Ser Asp Leu Gly Pro
            20                  25                  30

Gln Met Leu Arg Glu Leu Gln Glu Thr Asn Ala Ala Leu Gln Asp Val
        35                  40                  45

Arg Glu Leu Leu Arg Gln Gln Val Arg Glu Ile Thr Phe Leu Lys Asn
    50                  55                  60

Thr Val Met Glu Cys Asp Ala Cys Gly Met Gln Gln Ser Val Arg Thr
65                  70                  75                  80

Gly Leu Pro Ser Val Arg Pro Leu Leu His Cys Ala Pro Gly Phe Cys
                85                  90                  95

Phe Pro Gly Val Ala Cys Ile Gln Thr Glu Ser Gly Ala Arg Cys Gly
            100                 105                 110

Pro Cys Pro Ala Gly Phe Thr Gly Asn Gly Ser His Cys Thr Asp Val
        115                 120                 125
```

-continued

```
Asn Glu Cys Asn Ala His Pro Cys Phe Pro Arg Val Arg Cys Ile Asn
    130                 135                 140
Thr Ser Pro Gly Phe Arg Cys Glu Ala Cys Pro Pro Gly Tyr Ser Gly
145                 150                 155                 160
Pro Thr His Gln Gly Val Gly Leu Ala Phe Ala Lys Ala Asn Lys Gln
                165                 170                 175
Val Cys Thr Asp Ile Asn Glu Cys Glu Thr Gly Gln His Asn Cys Val
            180                 185                 190
Pro Asn Ser Val Cys Ile Asn Thr Arg Gly Ser Phe Gln Cys Gly Pro
        195                 200                 205
Cys Gln Pro Gly Phe Val Gly Asp Gln Ala Ser Gly Cys Gln Arg Arg
210                 215                 220
Ala Gln Arg Phe Cys Pro Asp Gly Ser Pro Ser Glu Cys His Glu His
225                 230                 235                 240
Ala Asp Cys Val Leu Glu Arg Asp Gly Ser Arg Ser Cys Val Cys Ala
                245                 250                 255
Val Gly Trp Ala Gly Asn Gly Ile Leu Cys Gly Arg Asp Thr Asp Leu
            260                 265                 270
Asp Gly Phe Pro Asp Glu Lys Leu Arg Cys Pro Glu Arg Gln Cys Arg
        275                 280                 285
Lys Asp Asn Cys Val Thr Val Pro Asn Ser Gly Gln Glu Asp Val Asp
290                 295                 300
Arg Asp Gly Ile Gly Asp Ala Cys Asp Pro Asp Ala Asp Gly Asp Gly
305                 310                 315                 320
Val Pro Asn Glu Lys Asp Asn Cys Pro Leu Val Arg Asn Pro Asp Gln
                325                 330                 335
Arg Asn Thr Asp Glu Asp Lys Trp Gly Asp Ala Cys Asp Asn Cys Arg
            340                 345                 350
Ser Gln Lys Asn Asp Asp Gln Lys Asp Thr Asp Gln Asp Gly Arg Gly
        355                 360                 365
Asp Ala Cys Asp Asp Ile Asp Gly Asp Arg Ile Arg Asn Gln Ala
370                 375                 380
Asp Asn Cys Pro Arg Val Pro Asn Ser Asp Gln Lys Asp Ser Asp Gly
385                 390                 395                 400
Asp Gly Ile Gly Asp Ala Cys Asp Asn Cys Pro Gln Lys Ser Asn Pro
                405                 410                 415
Asp Gln Ala Asp Val Asp His Asp Phe Val Gly Asp Ala Cys Asp Ser
            420                 425                 430
Asp Gln Asp Gln Asp Gly Asp Gly His Gln Asp Ser Arg Asp Asn Cys
        435                 440                 445
Pro Thr Val Pro Asn Ser Ala Gln Glu Asp Ser Asp His Asp Gly Gln
450                 455                 460
Gly Asp Ala Cys Asp Asp Asp Asp Asn Asp Gly Val Pro Asp Ser
465                 470                 475                 480
Arg Asp Asn Cys Arg Leu Val Pro Asn Pro Gly Gln Glu Asp Ala Asp
                485                 490                 495
Arg Asp Gly Val Gly Asp Val Cys Gln Asp Asp Phe Asp Ala Asp Lys
            500                 505                 510
Val Val Asp Lys Ile Asp Val Cys Pro Glu Asn Ala Glu Val Thr Leu
        515                 520                 525
Thr Asp Phe Arg Ala Phe Gln Thr Val Val Leu Asp Pro Glu Gly Asp
530                 535                 540
Ala Gln Ile Asp Pro Asn Trp Val Val Leu Asn Gln Gly Arg Glu Ile
```

-continued

```
                545                 550                 555                 560
Val Gln Thr Met Asn Ser Asp Pro Gly Leu Ala Val Gly Tyr Thr Ala
                    565                 570                 575
Phe Asn Gly Val Asp Phe Glu Gly Thr Phe His Val Asn Thr Val Thr
                580                 585                 590
Asp Asp Asp Tyr Ala Gly Phe Ile Phe Gly Tyr Gln Asp Ser Ser Ser
            595                 600                 605
Phe Tyr Val Val Met Trp Lys Gln Met Glu Gln Thr Tyr Trp Gln Ala
        610                 615                 620
Asn Pro Phe Arg Ala Val Ala Glu Pro Gly Ile Gln Leu Lys Ala Val
625                 630                 635                 640
Lys Ser Ser Thr Gly Pro Gly Glu Gln Leu Arg Asn Ala Leu Trp His
                    645                 650                 655
Thr Gly Asp Thr Glu Ser Gln Val Arg Leu Leu Trp Lys Asp Pro Arg
                660                 665                 670
Asn Val Gly Trp Lys Asp Lys Lys Ser Tyr Arg Trp Phe Leu Gln His
            675                 680                 685
Arg Pro Gln Val Gly Tyr Ile Arg Val Arg Phe Tyr Glu Gly Pro Glu
        690                 695                 700
Leu Val Ala Asp Ser Asn Val Val Leu Asp Thr Thr Met Arg Gly Gly
705                 710                 715                 720
Arg Leu Gly Val Phe Cys Phe Ser Gln Glu Asn Ile Ile Trp Ala Asn
                    725                 730                 735
Leu Arg Tyr Arg Cys Asn Asp Thr Ile Pro Glu Asp Tyr Glu Thr His
                740                 745                 750
Gln Leu Arg Gln Ala
        755

<210> SEQ ID NO 2
<211> LENGTH: 14
<212> TYPE: PRT
<213> ORGANISM: Homo sapiens

<400> SEQUENCE: 2

Asn Thr Val Met Glu Cys Asp Ala Cys Gly Met Gln Gln Ser
1               5                   10

<210> SEQ ID NO 3
<211> LENGTH: 22
<212> TYPE: PRT
<213> ORGANISM: Homo sapiens

<400> SEQUENCE: 3

Leu His Cys Ala Pro Gly Phe Cys Phe Pro Gly Val Ala Cys Ile Gln
1               5                   10                  15

Thr Glu Ser Gly Ala Arg
            20

<210> SEQ ID NO 4
<211> LENGTH: 20
<212> TYPE: PRT
<213> ORGANISM: Homo sapiens

<400> SEQUENCE: 4

Cys Ala Pro Gly Phe Cys Phe Pro Gly Val Ala Cys Ile Gln Thr Glu
1               5                   10                  15

Ser Gly Ala Arg
            20
```

```
<210> SEQ ID NO 5
<211> LENGTH: 11
<212> TYPE: PRT
<213> ORGANISM: Homo sapiens

<400> SEQUENCE: 5

Cys Val Pro Asn Ser Val Cys Ile Asn Thr Arg
1               5                   10

<210> SEQ ID NO 6
<211> LENGTH: 19
<212> TYPE: PRT
<213> ORGANISM: Homo sapiens

<400> SEQUENCE: 6

Gln Val Cys Thr Asp Ile Asn Glu Cys Glu Thr Gly Gln His Asn Cys
1               5                   10                  15

Val Pro Asn

<210> SEQ ID NO 7
<211> LENGTH: 10
<212> TYPE: PRT
<213> ORGANISM: Homo sapiens

<400> SEQUENCE: 7

Ser Val Cys Ile Asn Thr Arg Gly Ser Phe
1               5                   10

<210> SEQ ID NO 8
<211> LENGTH: 22
<212> TYPE: PRT
<213> ORGANISM: Homo sapiens

<400> SEQUENCE: 8

Gln Cys Gly Pro Cys Gln Pro Gly Phe Val Gly Asp Gln Ala Ser Gly
1               5                   10                  15

Cys Gln Arg Arg Ala Gln
            20

<210> SEQ ID NO 9
<211> LENGTH: 15
<212> TYPE: PRT
<213> ORGANISM: Homo sapiens

<400> SEQUENCE: 9

Ile Asp Val Cys Pro Glu Asn Ala Glu Val Thr Leu Thr Asp Phe
1               5                   10                  15

<210> SEQ ID NO 10
<211> LENGTH: 14
<212> TYPE: PRT
<213> ORGANISM: Homo sapiens

<400> SEQUENCE: 10

Thr Glu Ser Gly Ala Arg Cys Gly Pro Cys Pro Ala Gly Phe
1               5                   10

<210> SEQ ID NO 11
<211> LENGTH: 12
<212> TYPE: PRT
<213> ORGANISM: Homo sapiens

<400> SEQUENCE: 11
```

```
Asn Gln Gly Arg Glu Ile Val Gln Thr Met Asn Ser
 1               5                  10

<210> SEQ ID NO 12
<211> LENGTH: 16
<212> TYPE: PRT
<213> ORGANISM: Homo sapiens

<400> SEQUENCE: 12

Glu Ile Val Gln Thr Met Asn Ser Asp Pro Gly Leu Ala Val Gly Tyr
 1               5                  10                  15

<210> SEQ ID NO 13
<211> LENGTH: 19
<212> TYPE: PRT
<213> ORGANISM: Homo sapiens

<400> SEQUENCE: 13

Glu Ile Val Gln Thr Met Asn Ser Asp Pro Gly Leu Ala Val Gly Tyr
 1               5                  10                  15

Thr Ala Phe

<210> SEQ ID NO 14
<211> LENGTH: 12
<212> TYPE: PRT
<213> ORGANISM: Homo sapiens

<400> SEQUENCE: 14

Gly Asp Thr Glu Ser Gln Val Arg Leu Leu Trp Lys
 1               5                  10

<210> SEQ ID NO 15
<211> LENGTH: 8
<212> TYPE: PRT
<213> ORGANISM: Homo sapiens

<400> SEQUENCE: 15

Trp Phe Leu Gln His Arg Pro Gln
 1               5

<210> SEQ ID NO 16
<211> LENGTH: 12
<212> TYPE: PRT
<213> ORGANISM: Homo sapiens

<400> SEQUENCE: 16

Phe Tyr Glu Gly Pro Glu Leu Val Ala Asp Ser Asn
 1               5                  10

<210> SEQ ID NO 17
<211> LENGTH: 13
<212> TYPE: PRT
<213> ORGANISM: Homo sapiens

<400> SEQUENCE: 17

Cys Phe Ser Gln Glu Asn Ile Ile Trp Ala Asn Leu Arg
 1               5                  10

<210> SEQ ID NO 18
<211> LENGTH: 5
<212> TYPE: PRT
<213> ORGANISM: Homo sapiens

<400> SEQUENCE: 18
```

Gly Met Gln Gln Ser
1               5

<210> SEQ ID NO 19
<211> LENGTH: 5
<212> TYPE: PRT
<213> ORGANISM: Homo sapiens

<400> SEQUENCE: 19

Ser Val Arg Pro Leu
1               5

<210> SEQ ID NO 20
<211> LENGTH: 5
<212> TYPE: PRT
<213> ORGANISM: Homo sapiens

<400> SEQUENCE: 20

Arg Pro Leu Leu His
1               5

<210> SEQ ID NO 21
<211> LENGTH: 5
<212> TYPE: PRT
<213> ORGANISM: Homo sapiens

<400> SEQUENCE: 21

Val Ala Cys Ile Gln
1               5

<210> SEQ ID NO 22
<211> LENGTH: 5
<212> TYPE: PRT
<213> ORGANISM: Homo sapiens

<400> SEQUENCE: 22

Thr Gly Gln His Asn
1               5

<210> SEQ ID NO 23
<211> LENGTH: 5
<212> TYPE: PRT
<213> ORGANISM: Homo sapiens

<400> SEQUENCE: 23

Asn Cys Val Pro Asn
1               5

<210> SEQ ID NO 24
<211> LENGTH: 5
<212> TYPE: PRT
<213> ORGANISM: Homo sapiens

<400> SEQUENCE: 24

Gln Arg Arg Ala Gln
1               5

<210> SEQ ID NO 25
<211> LENGTH: 5
<212> TYPE: PRT
<213> ORGANISM: Homo sapiens

<400> SEQUENCE: 25

Thr Leu Thr Asp Phe

```
1               5

<210> SEQ ID NO 26
<211> LENGTH: 5
<212> TYPE: PRT
<213> ORGANISM: Homo sapiens

<400> SEQUENCE: 26

Asn Trp Val Val Leu
1               5

<210> SEQ ID NO 27
<211> LENGTH: 5
<212> TYPE: PRT
<213> ORGANISM: Homo sapiens

<400> SEQUENCE: 27

Leu Ala Val Gly Tyr
1               5

<210> SEQ ID NO 28
<211> LENGTH: 5
<212> TYPE: PRT
<213> ORGANISM: Homo sapiens

<400> SEQUENCE: 28

Gly Tyr Thr Ala Phe
1               5

<210> SEQ ID NO 29
<211> LENGTH: 5
<212> TYPE: PRT
<213> ORGANISM: Homo sapiens

<400> SEQUENCE: 29

Ala Leu Trp His Thr
1               5

<210> SEQ ID NO 30
<211> LENGTH: 5
<212> TYPE: PRT
<213> ORGANISM: Homo sapiens

<400> SEQUENCE: 30

Gln His Arg Pro Gln
1               5

<210> SEQ ID NO 31
<211> LENGTH: 5
<212> TYPE: PRT
<213> ORGANISM: Homo sapiens

<400> SEQUENCE: 31

Val Ala Asp Ser Asn
1               5

<210> SEQ ID NO 32
<211> LENGTH: 5
<212> TYPE: PRT
<213> ORGANISM: Homo sapiens

<400> SEQUENCE: 32

Arg Leu Gly Val Phe
1               5
```

<210> SEQ ID NO 33
<211> LENGTH: 5
<212> TYPE: PRT
<213> ORGANISM: Homo sapiens

<400> SEQUENCE: 33

Val Arg Thr Gly Leu
1               5

<210> SEQ ID NO 34
<211> LENGTH: 5
<212> TYPE: PRT
<213> ORGANISM: Homo sapiens

<400> SEQUENCE: 34

Leu His Cys Ala Pro
1               5

<210> SEQ ID NO 35
<211> LENGTH: 5
<212> TYPE: PRT
<213> ORGANISM: Homo sapiens

<400> SEQUENCE: 35

Cys Ala Pro Gly Phe
1               5

<210> SEQ ID NO 36
<211> LENGTH: 5
<212> TYPE: PRT
<213> ORGANISM: Homo sapiens

<400> SEQUENCE: 36

Thr Glu Ser Gly Ala
1               5

<210> SEQ ID NO 37
<211> LENGTH: 5
<212> TYPE: PRT
<213> ORGANISM: Homo sapiens

<400> SEQUENCE: 37

Cys Val Pro Asn Ser
1               5

<210> SEQ ID NO 38
<211> LENGTH: 5
<212> TYPE: PRT
<213> ORGANISM: Homo sapiens

<400> SEQUENCE: 38

Ser Val Cys Ile Asn
1               5

<210> SEQ ID NO 39
<211> LENGTH: 5
<212> TYPE: PRT
<213> ORGANISM: Homo sapiens

<400> SEQUENCE: 39

Arg Phe Cys Pro Asp
1               5

<210> SEQ ID NO 40

```
<211> LENGTH: 5
<212> TYPE: PRT
<213> ORGANISM: Homo sapiens

<400> SEQUENCE: 40

Arg Ala Phe Gln Thr
1               5

<210> SEQ ID NO 41
<211> LENGTH: 5
<212> TYPE: PRT
<213> ORGANISM: Homo sapiens

<400> SEQUENCE: 41

Asn Gln Gly Arg Glu
1               5

<210> SEQ ID NO 42
<211> LENGTH: 5
<212> TYPE: PRT
<213> ORGANISM: Homo sapiens

<400> SEQUENCE: 42

Thr Ala Phe Asn Gly
1               5

<210> SEQ ID NO 43
<211> LENGTH: 5
<212> TYPE: PRT
<213> ORGANISM: Homo sapiens

<400> SEQUENCE: 43

Asn Gly Val Asp Phe
1               5

<210> SEQ ID NO 44
<211> LENGTH: 5
<212> TYPE: PRT
<213> ORGANISM: Homo sapiens

<400> SEQUENCE: 44

Gly Asp Thr Glu Ser
1               5

<210> SEQ ID NO 45
<211> LENGTH: 5
<212> TYPE: PRT
<213> ORGANISM: Homo sapiens

<400> SEQUENCE: 45

Val Gly Tyr Ile Arg
1               5

<210> SEQ ID NO 46
<211> LENGTH: 5
<212> TYPE: PRT
<213> ORGANISM: Homo sapiens

<400> SEQUENCE: 46

Val Val Leu Asp Thr
1               5

<210> SEQ ID NO 47
<211> LENGTH: 5
<212> TYPE: PRT
```

<213> ORGANISM: Homo sapiens

<400> SEQUENCE: 47

Cys Phe Ser Gln Glu
1               5